(12) United States Patent
Liversidge

(10) Patent No.: US 10,179,210 B2
(45) Date of Patent: Jan. 15, 2019

(54) MEDICAL NEEDLE SAFETY DEVICE

(71) Applicant: tip-top.com Ltd., Stanway, Colchester, Essex (GB)

(72) Inventor: Barry Peter Liversidge, Colchester (GB)

(73) Assignee: TIP-TOP.COM LTD. (GB)

( * ) Notice: Subject to any disclaimer, the term of this patent is extended or adjusted under 35 U.S.C. 154(b) by 264 days.

(21) Appl. No.: 14/654,235

(22) PCT Filed: Dec. 19, 2013

(86) PCT No.: PCT/GB2013/053353
§ 371 (c)(1),
(2) Date: Jun. 19, 2015

(87) PCT Pub. No.: WO2014/096825
PCT Pub. Date: Jun. 26, 2014

(65) Prior Publication Data
US 2015/0343154 A1    Dec. 3, 2015

(30) Foreign Application Priority Data
Dec. 19, 2012  (GB) .................................. 1222900.1

(51) Int. Cl.
*A61M 5/32* (2006.01)
(52) U.S. Cl.
CPC ........ *A61M 5/3243* (2013.01); *A61M 5/3245* (2013.01); *A61M 2005/3247* (2013.01);
(Continued)
(58) Field of Classification Search
CPC .. A61M 2005/3247; A61M 2005/3267; A61M 2005/3268; A61M 5/3243;
(Continued)

(56) References Cited

U.S. PATENT DOCUMENTS

| 4,553,541 A | 11/1985 | Burns |
| 5,421,347 A | 6/1995 | Enström |

(Continued)

FOREIGN PATENT DOCUMENTS

| EP | 1558311 | 8/2004 |
| WO | 2008050158 | 5/2008 |

(Continued)

OTHER PUBLICATIONS

International Search Report for PCT/GB2013/053353 dated Mar. 31, 2014.

*Primary Examiner* — Deanna K Hall
(74) *Attorney, Agent, or Firm* — Grossman Tucker Perreault & Pfleger PLLC

(57) ABSTRACT

A medical needle safety device includes a needle mount for supporting the needle and a needle shielding sleeve surrounding a supported needle coaxially with the mount, for sliding from a needle shielding position towards a non-shielding position. The mount (30) provides a sliding surface and a resiliently flexible finger is provided on the sleeve, the finger being resiliently deformed outwardly as the sleeve moves towards a non-shielding position, to urge the sleeve back to a shielding position. A control member is disposed within the sleeve and the inner surface of the finger has a camming surface with a transition profile between the inner surface and canning surface. On initial rearward movement of the sleeve, the control member interacts with the camming surface of the finger to flex the finger outwardly and store energy therein. Further rearward movement of the sleeve transfers the inner surface of the finger on to the sliding surface of the mount whereby the stored energy in the finger urges the sleeve forwardly to the shielding position.

29 Claims, 25 Drawing Sheets

(52) U.S. Cl.
CPC ............... *A61M 2005/3267* (2013.01); *A61M 2005/3268* (2013.01)

(58) Field of Classification Search
CPC .......... A61M 5/3245; A61M 2005/208; A61M 5/31501; A61M 5/3157; A61M 5/3275; A61M 5/50; A61M 5/5086
See application file for complete search history.

(56) References Cited

U.S. PATENT DOCUMENTS

| | | |
|---|---|---|
| 2002/0087180 A1 | 7/2002 | Searle et al. |
| 2009/0227956 A1 | 9/2009 | Emmott et al. |

FOREIGN PATENT DOCUMENTS

| | | | |
|---|---|---|---|
| WO | 2011092518 | 8/2011 | |
| WO | WO 2011092518 A2 * | 8/2011 | ............ A61M 5/326 |
| WO | 2012073040 | 6/2012 | |
| WO | 2012095661 | 7/2012 | |

* cited by examiner

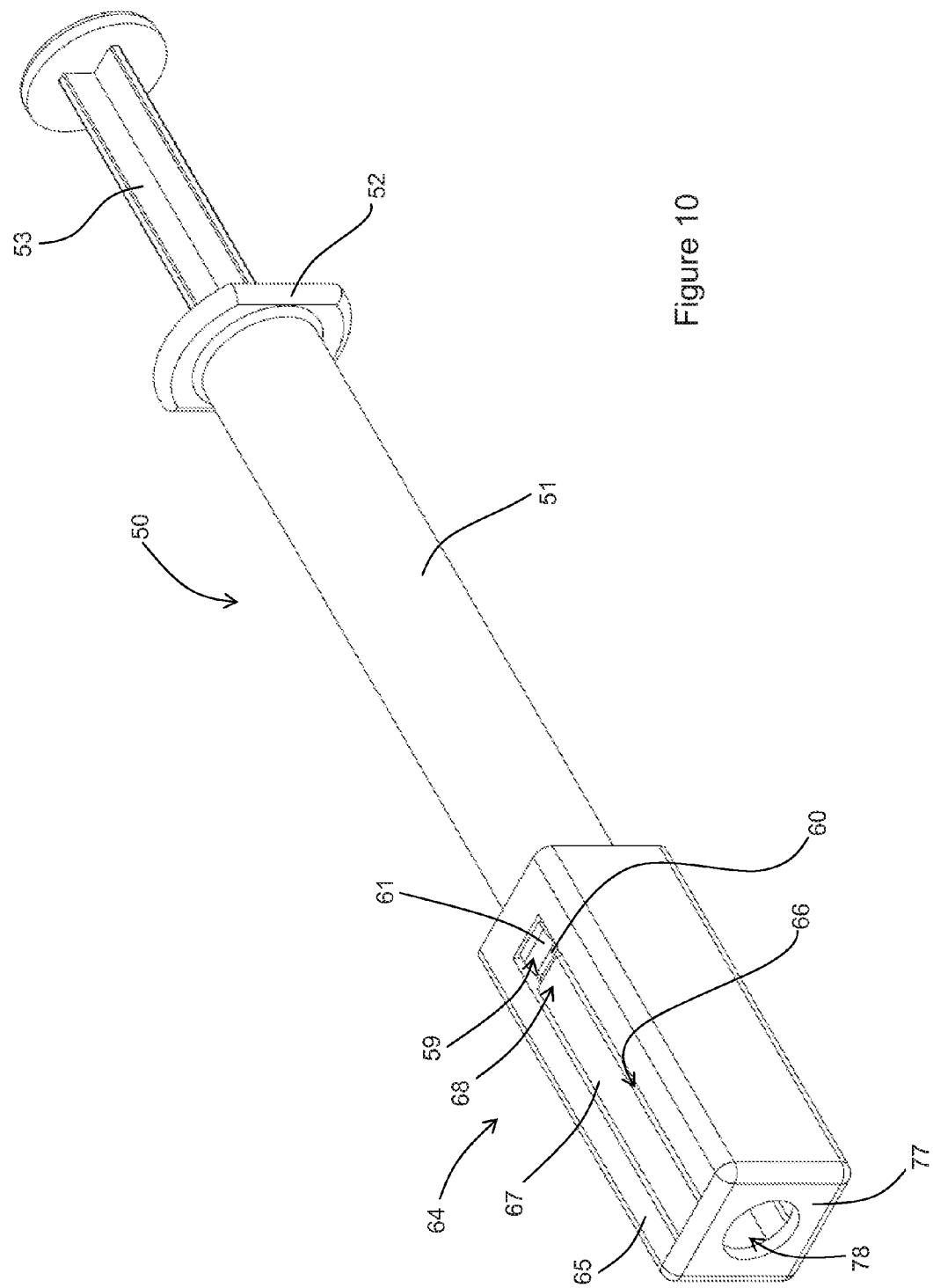

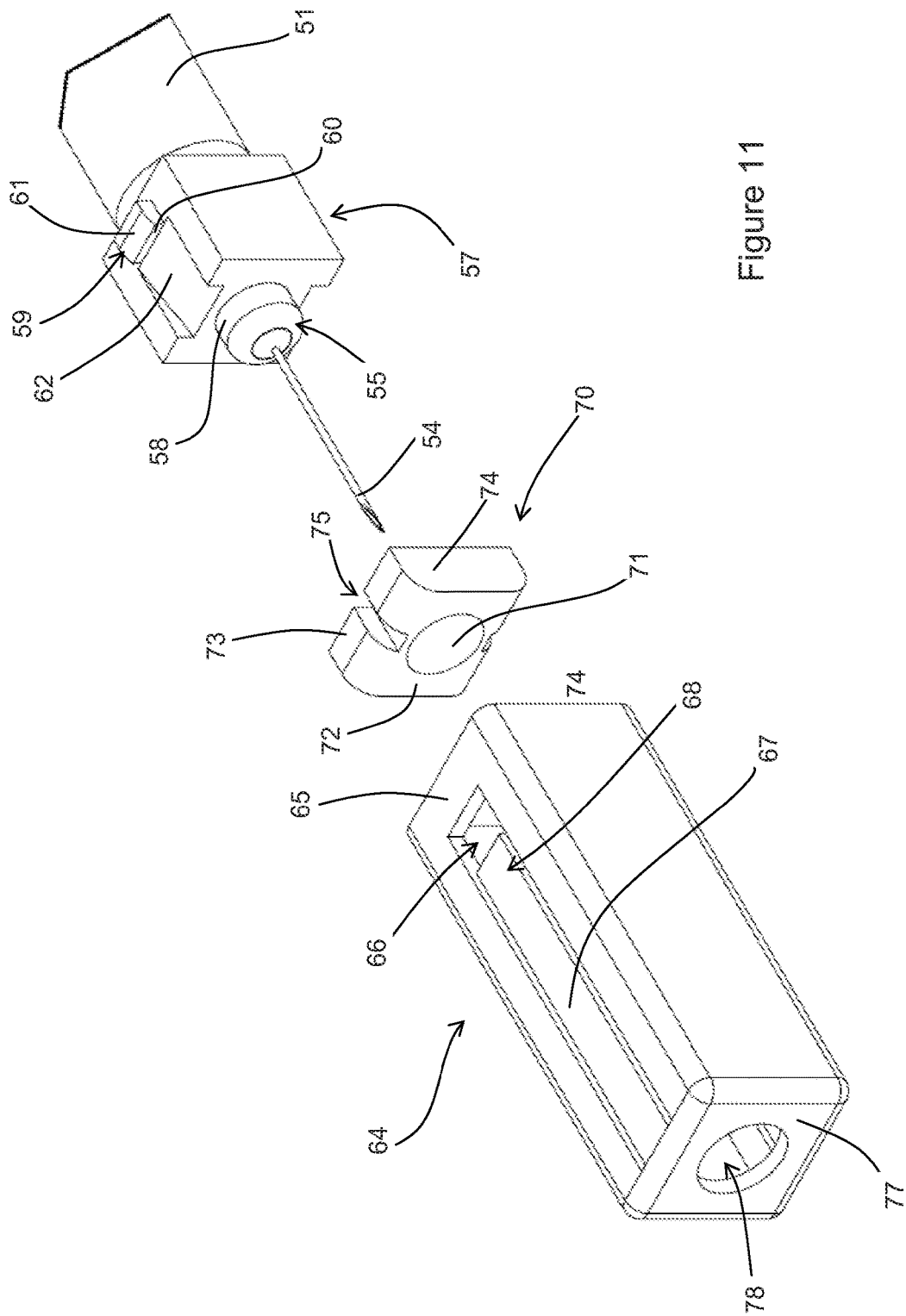

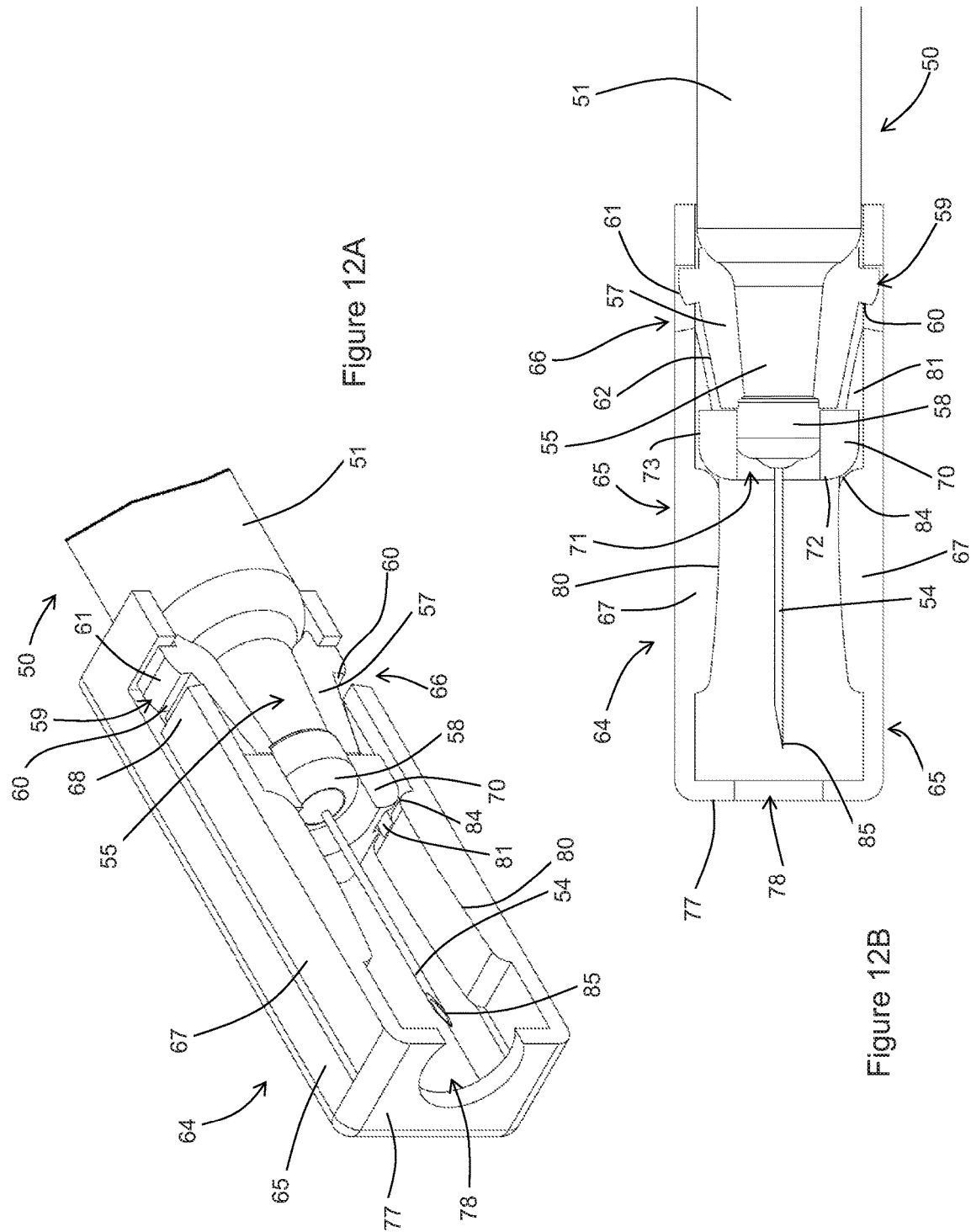

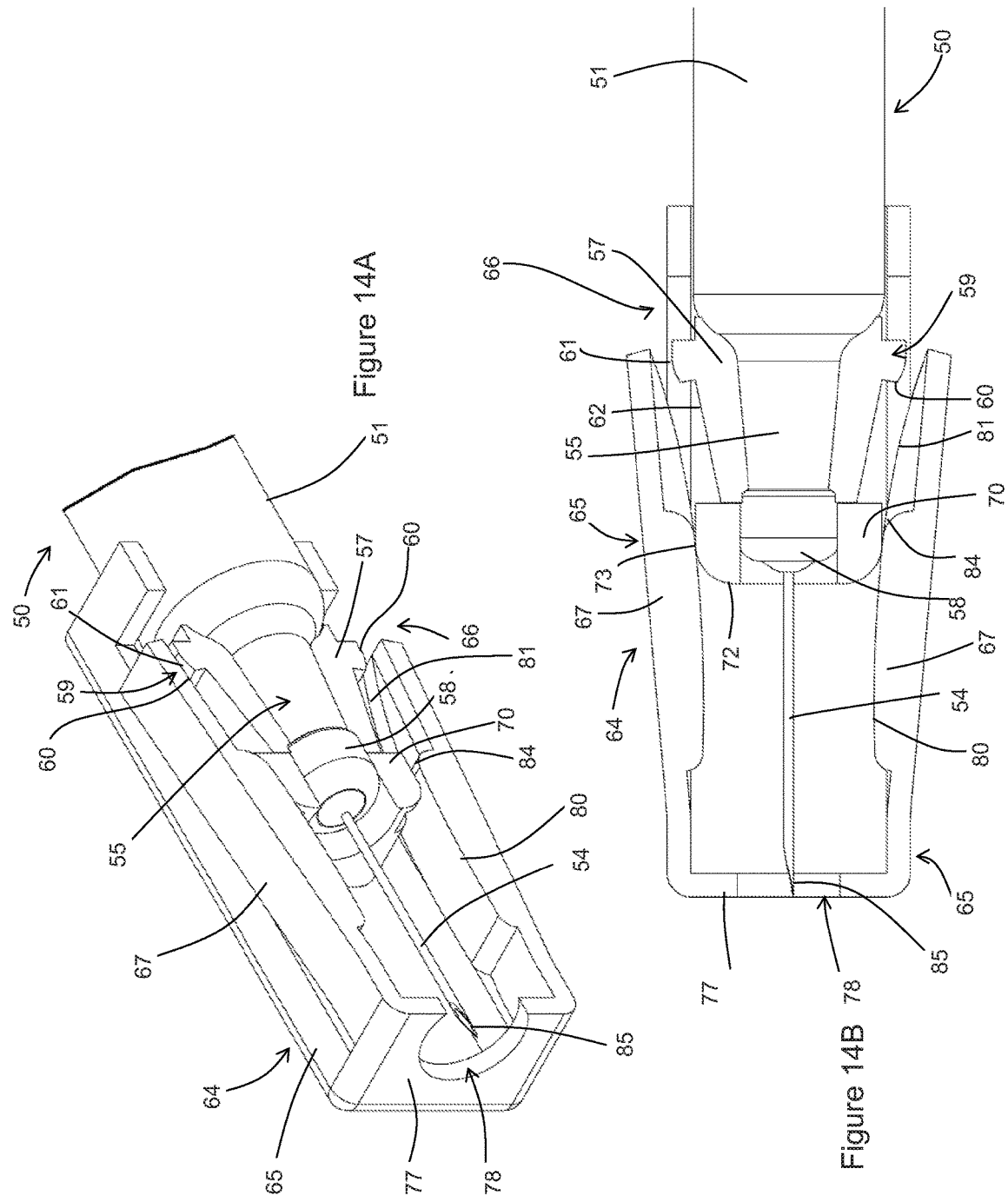

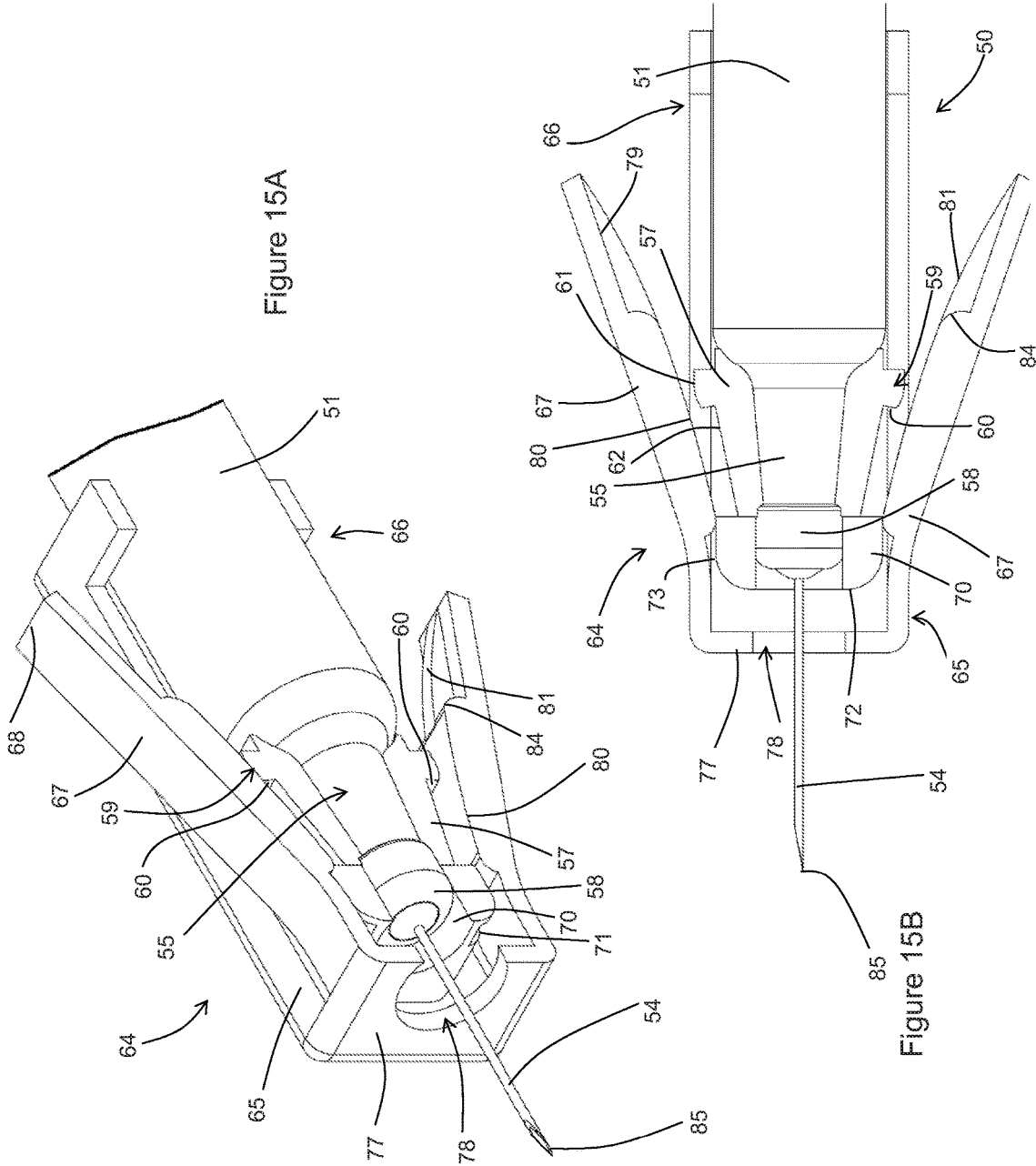

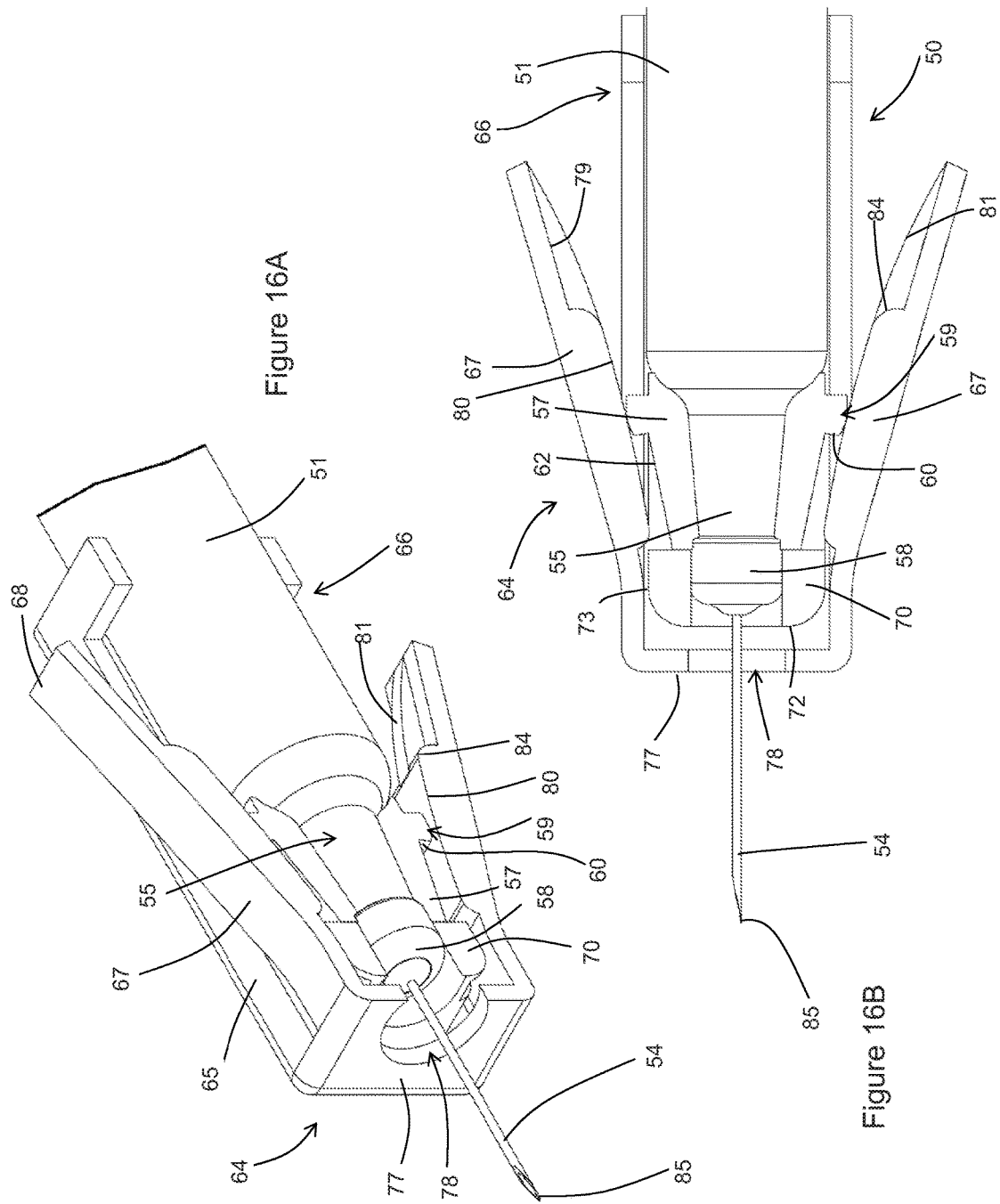

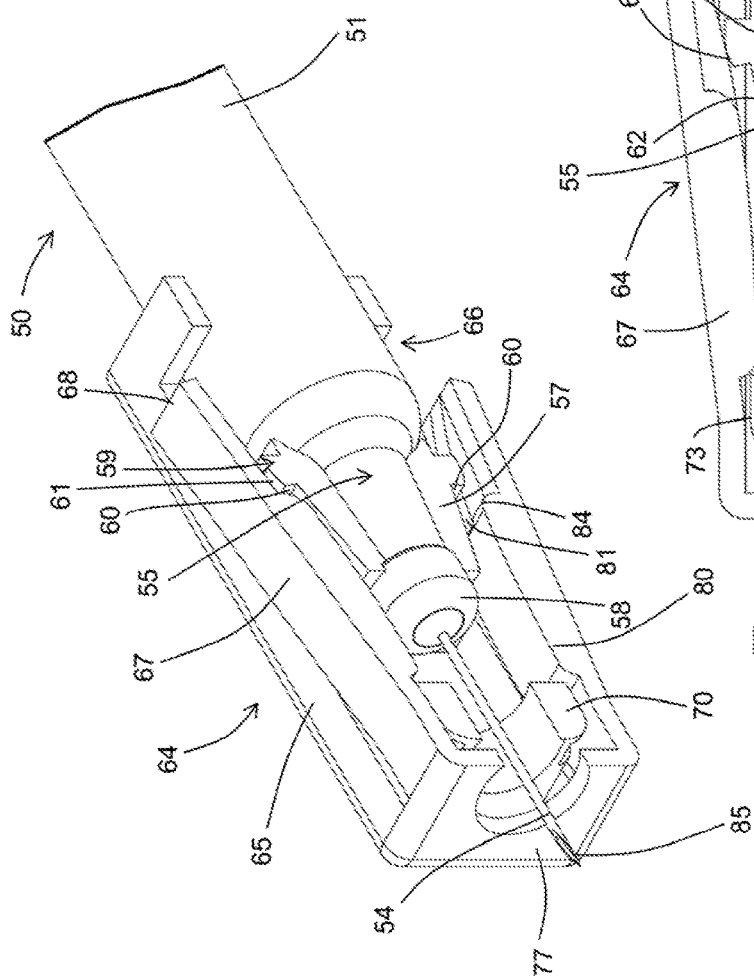

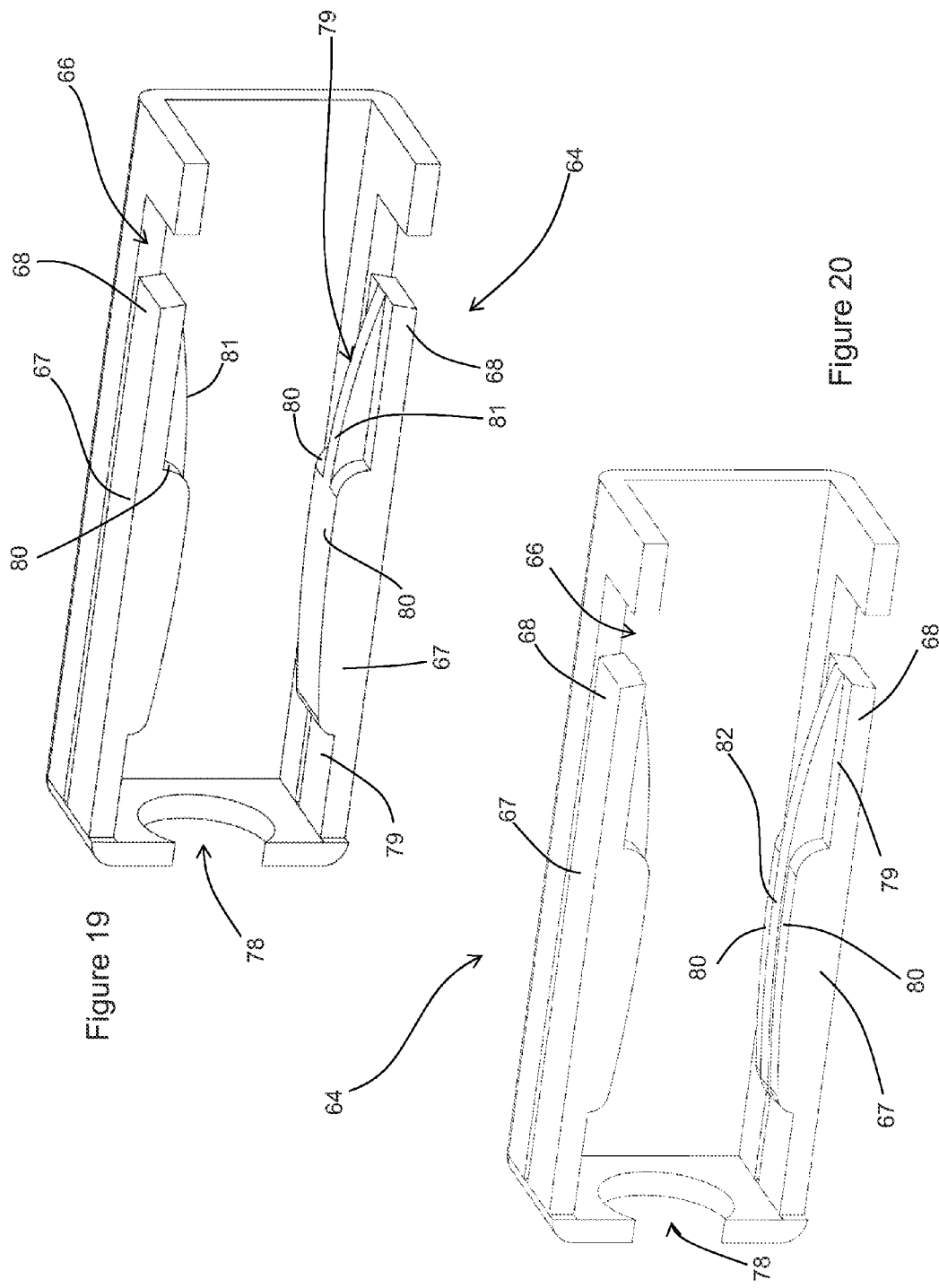

MEDICAL NEEDLE SAFETY DEVICE

CROSS REFERENCE TO RELATED APPLICATIONS

The present application is the U.S. national stage application of International Application PCT/GB2013/053353, filed Dec. 19, 2013, which international application was published on Jun. 26, 2014, as international Publication WO2014/096825. The International Application claims priority of British Patent Application 1222900.1, filed Dec. 19. 2012, the contents of which are incorporated herein by reference in their entireties.

FIELD

This invention relates to a safety device for use with a medical needle having a sharp tip, to confer passive protection to that needle. The invention also relates to a safety needle assembly including such a device and to an injection device incorporating such a safety needle assembly.

The safety device of this invention is intended for use with a medical needle (which may be incorporated as a part of the device) used to penetrate a human or animal body, or for other medical uses such as the penetration of a pierceable membrane of an intravenous medication system. In the following, all medical uses of the needle safety device will be described simply as the penetration of a body, even though specific embodiments may be intended for other medical uses.

Throughout this specification the terms "forward" and "forwardly" used in relation to the needle safety device and a syringe for use therewith refer to those ends of the components which are approached towards a body when a procedure is to be performed, and the direction towards those ends. Conversely, the terms "rearward" and "rearwardly" refer to those ends of the components opposed to the forward ends and the direction away from those forward ends.

BACKGROUND

Fluids of various kinds may be administered to a body by means of a hollow needle in conjunction with a source of the required fluid. For example, such a needle may be associated with a syringe holding a liquid drug, the needle being used to penetrate the body at the site at which the drug is to be administered. Equally, body fluids may be withdrawn by using a hollow needle which is used to penetrate the body until the tip is located at the site from which fluid is to be withdrawn.

A recognised hazard for clinicians and other persons using or handling medical needles for the above described purposes is the risk of a so-called needle-stick injury—that is to say the accidental penetration of another's skin by the needle. Prior to the use of the needle to supply a fluid to or to withdraw fluid from a body, this rarely presents much of a problem, though once the needle has been used, there is a very much higher risk of a serious consequence for the clinician, or others associated with the disposal of a used needle. During use of the needle to penetrate the body tissues of a patient, the needle is likely to become contaminated with various organisms; should someone subsequently suffer a needle-stick injury, infection could occur.

There have been numerous proposals for protecting the sharp tip of a used needle, in order to reduce the risk of a needle-stick injury following use of the needle. Some proposals have actually increased the likelihood of such an injury by virtue of the action which must be performed to protect the tip, even if the risk thereafter is lessened. Despite all of the proposals which have previously been made, very few have achieved commercial success, nor has there been wide acceptance by the medical industry. Many proposals are somewhat complex and involve a significantly greater manufacturing cost, and so are unacceptable on economic grounds. Others are much more difficult to use as compared to an unprotected needle, and so are rejected by clinicians. Yet further proposals do not allow compliance with best practice protocols.

A device which protects a needle tip after use without an operator having to perform any extra step on withdrawing the needle from a body is usually referred to as a passive protection device. This may be contrasted with an active protection device, where an operator is required to perform an extra step in order to protect a needle, following the withdrawal of the needle from a body. The requirement to perform an extra step leaves the needle unprotected for a longer period than with a passive protection device and further the performance of that extra step exposes the operator to a potentially hazardous situation, when needle-stick accidents can occur.

There is a significant demand for a passive protection device for use with a needle and which allows a clinician or perhaps others to use the needle in much the same way as is done with an unprotected needle, but which can be manufactured economically and which provides a high degree of protection against needle-stick injury. In the case of health professionals, this demand is driven by health and safety legislation but in the case of others performing self-injections using a so-called pen injector, the used needles must be disposed of safely with minimum risk to others, even in the event that a sharps container is not immediately available. Further, particularly for self-injections, it is highly preferred that the device operates fully automatically, without intervention by the user, so as wholly to prevent access to the needle tip both before and after use, other than by a determined attempt to override the protection. In this way, protection may be afforded not just to the clinician or other user of the needle, but also to people who could come into a risky situation with used needles, such as waste disposal operators, cleaners, and so on.

Passive protection devices mostly have used metal helical coil springs to urge a protecting sleeve forwardly to a protecting position over a needle, but this in general adds to the cost of a device, which is of course a throw-away item, once used. The cost may be reduced by moulding an integral plastics material spring with a component of the device, but this leads to difficulties associated with creep of plastics materials stored when stressed. These can be alleviated to some extent by using leaf springs running on surfaces inclined to the needle axis. Early designs can be found in U.S. Pat. Nos. 4,553,541, 5,421,347 and US 2002/0087180. A more recent development, directed to protecting an injection needle, is described in EP1558311 (Salvus Technology).

Another such device has been described in WO2011/092518 (Liversidge). This provides a simple, easy to use and economically viable safety device, conferring passive protection to the needle. The device of WO2011/092518 may be moulded from plastics materials and does not require the use of metal springs, as the device addresses the known problem of a plastic spring in that if the spring is stored in a stressed condition, there is a likelihood that the spring will lose at least some of its resilience and so may not be able to return to its as-manufactured unstressed condition. Though the device of WO2011/092518 incorporates a plastic spring, it is designed to be stored with the spring in a substantially unstressed condition but is able to operate effectively and reliably, to give passive needle-stick protection.

It is a feature of the device of WO2011/092518 that as soon as the needle shielding sleeve has been moved through a small distance from its needle shielding position, release of the sleeve will result in the device locking-out, so preventing subsequent movement of the sleeve from its needle protecting position. It is however sometimes highly advantageous for a user of the device to be able to move the sleeve to expose the sharp tip of the needle before actually performing an medical procedure, for example for aspirating the syringe to which the needle is attached, or perhaps for drawing a drug into the syringe. Such action is not possible with the device of WO2011/092518.

SUMMARY

It is an aim of this invention to provide a medical needle safety device similar to that of WO2011/092518, but in which, depending upon the precise configuration of the device, the needle shielding sleeve will not be returned to a shielding position and locked there in the event that the sleeve is moved from an initial shielding position through a relatively small distance to expose at least the tip of the needle; and further to maintain the sleeve at an intermediate position, whereby a medical procedure may thereafter be performed. Preferred forms of this invention permit the performance and operation of the device to be controlled during the manufacture of the device, thereby to facilitate uses in different circumstances, or for different purposes.

According to a first aspect of this invention there is provided a safety device for shielding a medical needle having a sharp tip, which device comprises:
  a needle mount for directly or indirectly supporting the safety device with respect to the medical needle;
  a needle shielding sleeve for surrounding the needle and arranged coaxially with the mount for sliding rearward movement relative to the mount from a needle shielding position towards a non-shielding position whereat at least the tip of the needle is exposed beyond the sleeve;
  a sliding surface provided on one of the sleeve and mount;
  at least one elongate resiliently flexible finger provided on the other of the sleeve and mount and serving as a spring to return the sleeve to a needle shielding position, the finger having an inner surface; and
  a control member having an outer surface and arranged coaxially with the sleeve and mount, the control member having an initial set position with respect to the finger and being slidably displaceable with respect to the finger from said set position when the sleeve slides towards the non-shielding position; wherein the inner surface of the finger is provided with an elongate camming surface and there being a transition profile between the camming surface and the inner surface; such that:
  rearward movement of the sleeve to the non-shielding position displaces the control member from its initial set position with respect to the finger so that the outer surface of the control member interacts with the camming surface of the finger, thereby flexing the finger to generate and store energy therein for returning the sleeve to a needle shielding position;
  and thereafter further rearward movement of the sleeve further displaces the control member so that the outer surface of the control member interacts with the transition profile of the finger, whereby the inner surface of the finger is transferred on to the sliding surface, the stored energy in the finger then acting on the sliding surface thereby to exert a spring force for returning the sleeve to a needle shielding position.

According to a second aspect of this invention, there is provided a safety device for shielding a medical needle having a sharp tip, which device comprises a needle mount for directly or indirectly supporting the safety device with respect to the medical needle and a needle shielding sleeve for surrounding the needle and arranged coaxially with the mount for sliding movement relative to the mount from an initial needle shielding position towards a non-shielding position whereat at least the tip of the needle is exposed beyond the sleeve. An abutment surface and a sliding surface are provided on one of the sleeve and mount, and at least one elongate resiliently flexible finger is provided on the other of the sleeve and mount and serving as a spring to return the sleeve to a needle shielding position, the finger having a part for engaging the abutment surface to block movement of the sleeve to the non-shielding position when said part is aligned and engaged with the abutment surface, the finger further having an inner surface and an elongate camming surface provided on the inner surface. A control member having an outer surface is arranged coaxially with the sleeve and mount, the control member having an initial set position with respect to the finger and being slidably displaceable with respect to the finger from said set position when the sleeve slides from its initial position towards a non-shielding position. In the safety device initial movement of the sleeve from its initial position displaces the control member from its set position so that the outer surface of the control member interacts with the camming surface of the finger to flex the finger and move said part thereof out of alignment with the abutment surface to allow the sleeve to move towards a non-shielding position. Continued movement of the sleeve to a non-shielding position causes continuing interaction between the control member and the camming surface to further increase the flexing of the finger so storing energy therein for returning the sleeve to a needle shielding position; and thereafter further movement of the sleeve exposes more of the needle beyond the sleeve and the interaction between the outer surface of the control member and the camming surface causes the inner surface of the finger to bear on said sliding surface so that the energy stored within the finger exerts a spring force on the sleeve, to urge the sleeve to a needle shielding position whereat said finger part is aligned with the abutment surface to block movement of the sleeve towards the non-shielding position.

The operation of the device may be tuned to have a chosen operational characteristic or function, by appropriate selection of the materials of the needle mount, the control member, the finger and the surface finishes and profiles of those interacting components. For example, by having a relatively high friction between the camming surface of the finger and the external surface of the control member, movement of the sleeve from its initial shielding position towards its non-shielding position will prevent the flexed finger urging the sleeve forwardly relative to the control member while the camming surface of the finger remains engaged with the external surface of the control member. When an inner surface of the finger or a camming surface is transferred to the sliding surface of the needle mount, which may have a low-friction finish, the finger may then urge the sleeve forwardly to its shielding position so long as there is a suitable degree of friction between the finger camming surface and the sliding surface of the needle mount. Adjustment of the point at which the transfer takes place will control the amount of needle which is exposed beyond the sleeve following displacement of the sleeve from its shielding position, before energy stored in the deformed finger starts to urge the sleeve forwardly.

Advantageously, the transition profile comprises a rounded or tapering surface extending along the length of the finger between the camming surface and the inner surface of the finger, whereby the camming surface slides off the control member outer surface when the transition profile slides on to the control member outer surface.

In a similar way, the profiles of the external outer surface of the control member and the sliding surface of the needle mount that are contacted by an inner surface or the camming surface of the finger may also be adjusted. These profiles may be rounded to a greater or lesser extent or may be relatively angular, thereby changing the frictional characteristics of the camming surfaces of the finger on those profiles. In turn this may allow the operation of the device to be easily and cost effectively controlled during the manufacture of the device, for use in different circumstances.

The spring force for returning the sleeve to a needle shielding position is generated by the rearward movement of the sleeve, flexing the finger (or each finger, where two or more are provided) so as to store energy therein consequent upon the interaction of an inner surface of the finger with the control member. Subsequently the sleeve is returned to a shielding position, when the energy within the stressed finger urges the sleeve forwardly with respect to the needle, until the sleeve once more is in a shielding position.

It will be appreciated that the safety device of this invention may be configured to allow considerable movement of the sleeve from its shielding position towards a non-shielding position, without the device operating to block movement of the sleeve if then returned to a shielding position. In the alternative, the device may be configured to allow the sleeve to remain stationary indefinitely at an intermediate position, displaced from the initial position. This can be advantageous when, for example, a user is to view the sharp tip of the needle for the purpose of aspirating the syringe, or better visual access to the needle tip for easier positioning of the needle. In either case, when the sleeve has subsequently been moved fully to perform an injection, the automatic return of the sleeve to its shielding position ensures that the sleeve is then blocked in that position, to render the needle safe and prevent re-use.

In one embodiment the device is preferably configured for use with a syringe having a needle permanently fitted thereto during manufacture. Such a syringe is often pre-filled with medicament and is used to dispense a single dose of that medicament before being disposed of in a safe manner.

The term "needle mount" as used herein may extend to a needle hub carrying a needle as described above, or may comprise a formation at the forward end of a syringe with a needle permanently fitted in the formation. The needle mount may be associated with a carrier for the needle and may be a part thereof or may be directly or indirectly mounted thereon; for example in the case of a syringe having a needle secured thereto, the needle mount may be mounted on the formation at the forward end of a syringe. Any of these needle mount arrangements are possible, so long as the needle shielding sleeve is arranged for sliding movement with respect to a needle for use in a medical procedure whereby a force applied to the forward end of the sleeve when in its initial position (for example by being pressed against the skin at an injection site) slides the sleeve rearwardly relative to the needle mount, thereby exposing at least a part of the length of the needle, back from its sharp tip. Though exposed beyond the sleeve, in use the needle will actually have penetrated the injection site and in fact it is the syringe and needle which is moved forwardly relative to the sleeve while the sleeve remains stationary bearing on the skin of a patient.

For convenience, the following description of preferred aspects of the invention will refer to a device having a single resiliently flexible finger, but a practical embodiment of the device will have typically two, three or even more resiliently flexible fingers each serving in effect as a leaf spring and circumferentially spaced around the component carrying the fingers. In a case where there are at least two fingers, both or all the fingers may be essentially the same.

In a modified form of this invention, the safety device is provided with at least two resiliently flexible fingers having distinct functions. One finger may perform the function of blocking rearward movement of the sleeve once the sleeve has moved from its protecting position to a non-protecting position where the needle is exposed and is then returned to a protecting position. The second finger may be resiliently flexed as the sleeve is moved rearwardly to store energy for returning the sleeve to a protecting position when the sleeve has been moved rearwardly to a non-protecting position, to expose the needle. Thus the second finger may have a camming surface provided on its inner surface, for interaction with the control member, as has been described hereinbefore. In this way, the interaction of the second finger along with its spring characteristics can be selected separately from the strength requirements for the one finger which serves the blocking function for the sleeve. The one finger may also be flexed to store energy as the sleeve moves to a non-protecting position, to contribute to the total force urging the sleeve forwardly from a non-shielding position to a shielding position. In this embodiment, the one and second fingers may be arranged closely adjacent each other or may be spaced around the axis of the device.

In one embodiment, the resiliently flexible finger comprises a part of the sleeve and has an essentially undeformed condition (i.e. in the case of a plastics finger, as moulded and so in an unstressed condition) in which relative movement of the sleeve rearwardly with respect to the needle mount is blocked by the finger engaging the abutment surface, unless said part of the finger has been moved out of alignment with the abutment surface. This will occur by the finger co-operating and interacting with the control member when the sleeve is moved from its needle shielding position.

Though in preferred embodiments the finger is moulded integrally with the sleeve, it would be possible to manufacture the finger as a separate item which is then attached or otherwise associated with the sleeve. This allows for different plastics or other materials to be used for the sleeve and the finger; for example it would be possible to make the finger as a leaf spring from a suitable metal.

When the finger is engaged with the outer surface of the control member, rearward movement of the sleeve is possible with the camming surface of the finger running on that outer surface. This causes resilient flexing of the finger outwardly with respect to the axis of the device (and with a cylindrical device, in a generally radially outward direction), so storing energy in the finger. So long as the sleeve has moved sufficiently rearwardly for the inner surface of the finger to be transferred to the needle mount, release of a rearward force on the sleeve (usually by moving the syringe, needle mount and needle rearwardly with respect to the injection site while the sleeve remains stationary engaged with that site) will allow the sleeve to move forwardly with respect to the needle mount, the energy stored in the finger serving to move the sleeve back to its shielding position, rather than remaining stationary with respect to the needle. The resilient finger, when contacting or acting on the needle mount, thus serves as a spring urging the sleeve to its needle shielding position.

The control member preferably is provided within the sleeve to flex the finger during rearward movement of the sleeve with respect to the needle mount towards a non-shielding position, so as to move said part of the finger out of alignment with the abutment surface. Thereafter, continued rearward movement of the sleeve increases the deflection of the finger by the camming surface thereof bearing on the outer surface of the control member so storing more energy by the resilient deformation thereof.

The control member is initially located relative to the sleeve and needle mount at a set position with the camming surface of the finger adjacent or contacting the control member. Then, on rearward movement of the sleeve, the co-operation or interaction of the finger camming surface with the outer surface of the control member flexes the finger to move said part of the finger out of alignment with the abutment surface, but simultaneously stores energy in the finger by virtue of the flexing thereof from its relaxed condition and in the case of a plastics spring, its as-moulded condition. Continuing rearward movement of the sleeve is thereafter possible, and the interaction of the surface camming and outer surface further flexes the finger outwardly thereby increasing the amount of energy stored therein. Eventually, when the sleeve has moved rearwardly to a sufficient extent, the control member having been displaced from its set position is located and received in a forward part of the sleeve and the inner surface of the finger is transferred to the sliding surface of the needle mount. The control member is retained in a forward part of the sleeve, so that on subsequent return of the sleeve to a needle shielding position by the action of the finger on the sliding surface, the control member is no longer located at its set position. If then an attempt is made to move the sleeve rearwardly, either deliberately or accidentally, said part of the finger will engage the abutment surface and block rearward sleeve movement.

In most preferred embodiments the finger has one end mounted on the sleeve and at the other end the finger defines said part for engaging the abutment surface of the needle mount, when the finger is not flexed and is in a substantially undeformed condition. The abutment surface may comprise a shoulder formed on the needle mount, preferably on a lug upstanding therefrom. Said part of the finger and the abutment surface may be profiled so as to minimise the likelihood of said part of the finger moving or sliding away from the abutment surface in the event that the sleeve is pushed rearwardly.

In embodiments of this invention, the eventual needle shielding position of the sleeve, relative to the mount and when blocked against rearward movement, may be essentially the same as the needle shielding position of the sleeve before use of the device, or may differ slightly from that before-use position. In some embodiments the sleeve may have a small degree of freedom of movement in the axial direction when in its shielding position. In such a case, the before-use position of the sleeve could be towards or at one extreme of that freedom of movement and the after-use position towards or at the other extreme of that freedom of movement. Despite this possible variation in the before-use and after-use positions of the sleeve, the after-use position will be substantially the same as the before-use position and functionally will be the same, in that in both positions the needle is shielded by the sleeve. Thus, it will be appreciated that the before-use shielding position of the sleeve and the after-use shielding position thereof may in fact be the same axial position.

Before use of an embodiment of the device, it may be preferred for there to be a sufficient clearance between said part of the finger which engages the abutment surface and the abutment surface itself, to allow enough relative movement between the finger and the control member for said part of the finger to be moved by the control member, clear of the abutment surface during first movement of the sleeve. On return of the sleeve to its needle shielding position, there will still be clearance between said part of the finger and the abutment surface when the sleeve is fully forward, but if an attempt is made to move the sleeve rearwardly, the finger will not be flexed by the control member, as the control member is no longer at its set position. Thus, blocking of the sleeve will take place by the action of said part of the finger engaging the abutment surface.

The control member may serve as an indicator to show whether the device is ready for use or has been used and the sleeve is blocked against sliding movement with respect to the mount. To enhance this, the control member may be of a color which contrasts with that of the sleeve and needle mount. A window may be provided in the coaxial arrangement of sleeve and needle mount within which the control member is slidably carried, said window being at the axial position of the sleeve to which the control member is moved when the sleeve is in its non-shielding position, whereby the control member may be observed through that window. Another possibility is for the sleeve to be of a translucent material whereby the position of the control member therewithin may be observed.

This invention extends to a needle safety device of this invention as discussed above in combination with a medical needle projecting forwardly from the needle mount, and also to an injection device fitted with the combination of the safety device and a medical needle.

BRIEF DESCRIPTION OF THE DRAWINGS

By way of example only, certain specific embodiments of this invention will now be described in detail, reference being made to the accompanying drawings in which:

FIG. 10 is an isometric view of a syringe having a second embodiment of safety device of this invention mounted on the syringe;

FIG. 11 is a view of the device of FIG. 10 but exploded to show the component parts;

FIGS. 12A and 12B are respectively a cut away isometric view and an axial sectional view of the device of FIGS. 10 and 11;

FIGS. 13A and 13B, 14A and 14B, 15A and 15B, 16A and 16B, 17A and 17B and 18A and 18B show sequential stages of the operation of the second embodiment of FIGS. 10 and 11, starting from the position of FIGS. 12A and 12B and ending with the sleeve in a needle protecting position as shown in FIGS. 18A and 18B;

FIG. 19 is a partly cut away view of the sleeve of the second embodiment, showing the internal surfaces of the fingers;

FIG. 20 is a partly cut away view of an alternative sleeve, showing a different configuration for the internal surfaces of the fingers;

DETAILED DESCRIPTION OF THE DRAWINGS

Figure 1:
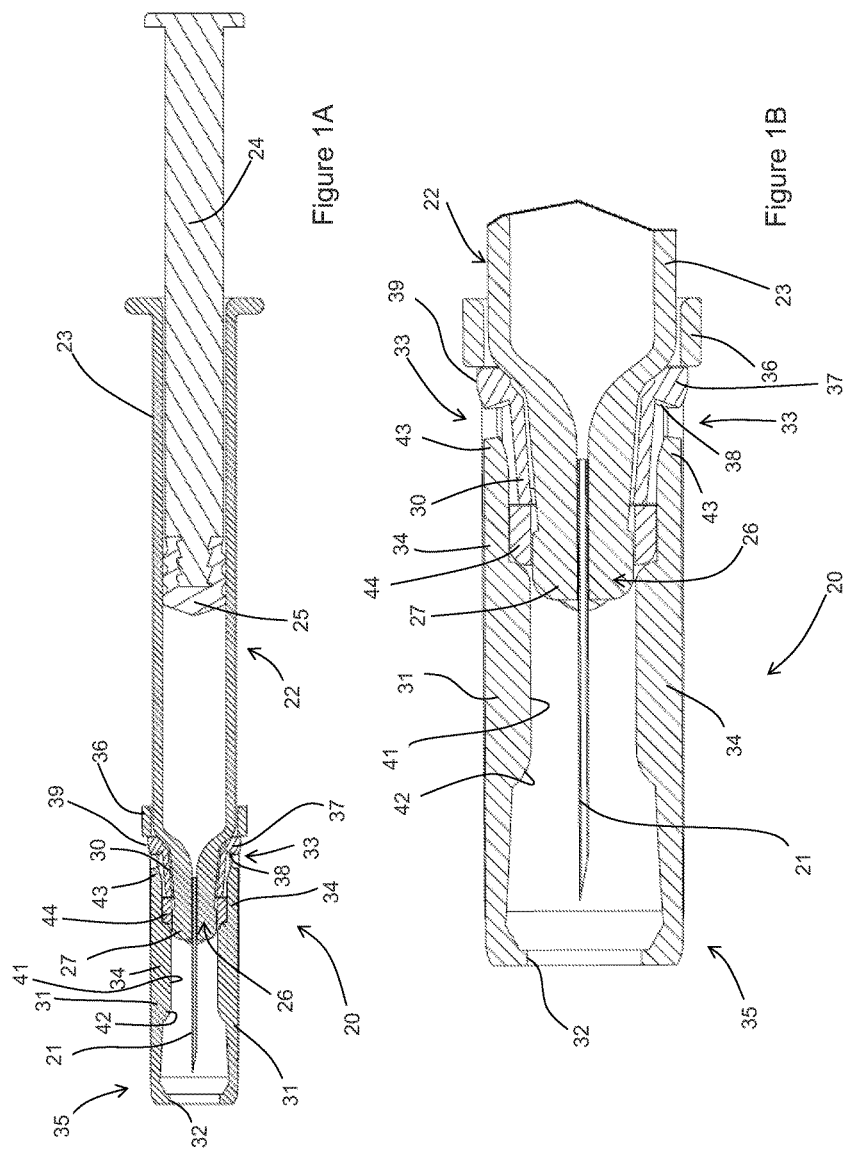
FIG. 1A is an axial cross-section through a first embodiment of safety device of this invention mounted on a single-use syringe having a needle attached thereto, with the device in an initial, ready-to-use setting and the sleeve in a shielding position.
FIG. 1B is an axial cross-section on an enlarged scale through the safety device shown in FIG. 1A, in an initial setting, the syringe being shown only in part.

Referring to FIGS. 1 to 8 of the drawings, there is shown a first embodiment of safety device 20 arranged for shielding a medical hollow needle 21 secured to a conventional form of single-use syringe 22. The syringe has a cylindrical body 23, usually of glass or plastic and defining a cylindrical chamber for a liquid medicament, there being a piston 25 fitted with a plunger 24 to expel medicament out of the needle 21 mounted in the syringe nose cone 26. That nose cone has an external surface formed with an enlargement 27 at the forward end thereof. Typically, a hard or soft needle cover is fitted to the needle, both to maintain sterility and prevent leakage from the needle. Such a syringe is entirely conventional and will not be described in further detail here.

The safety device 20 has a needle mount 30 provided with a bore which is adapted to be a close push-fit on the nose cone 26 of the syringe, by being snapped over the enlargement 27. A sleeve 31 is arranged on the needle mount 30 for axial sliding movement with respect thereto and so also with respect to the syringe 22 and needle 21. The sleeve has an in-turned lip 32 at its forward end with a sufficiently large hole to allow a needle shield (not shown in any of the drawings) to pass therethrough.

Figure 5:
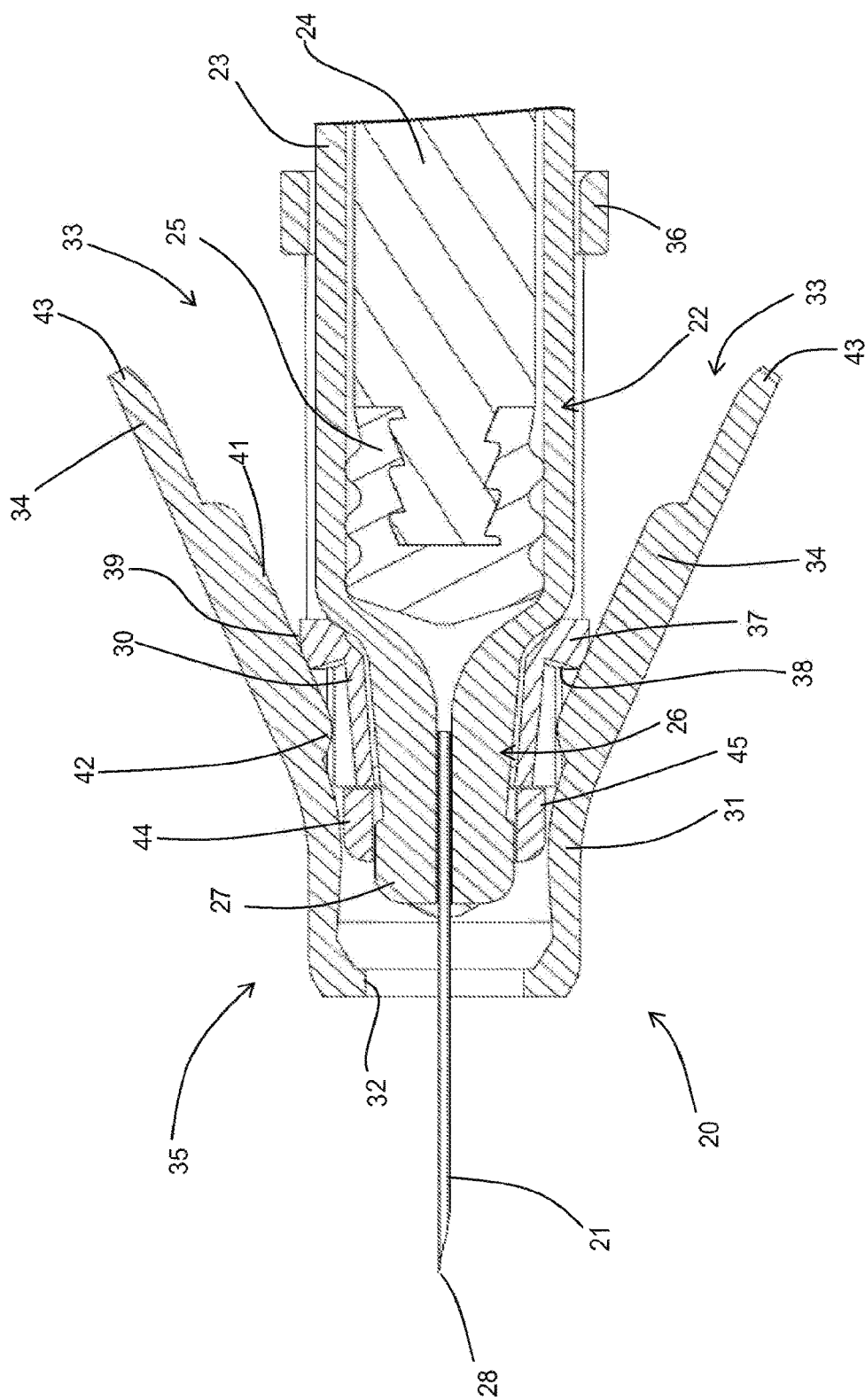
Figure 6:
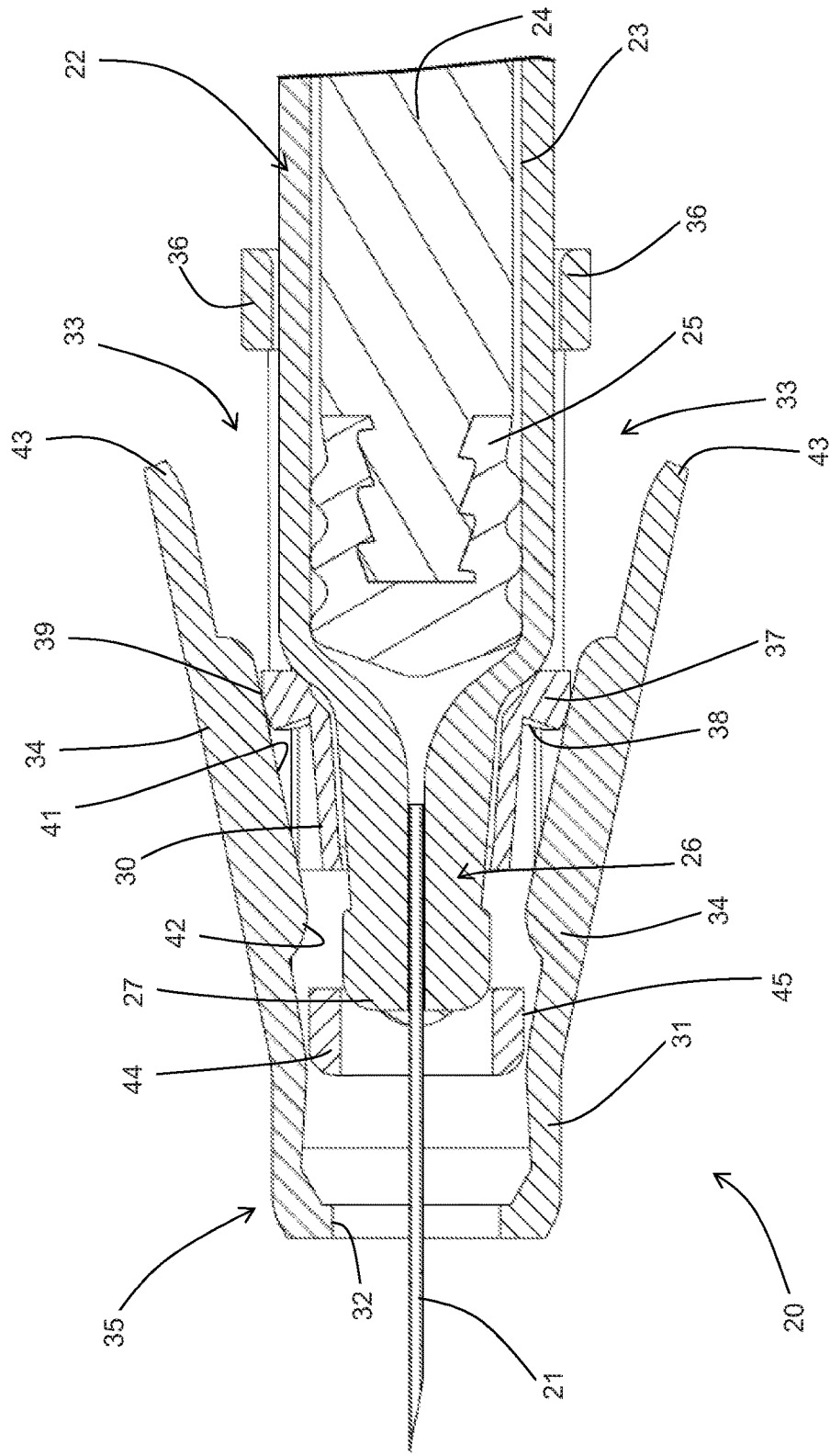
FIG. 6 is similar to FIG. 5 but showing the returning movement of the sleeve, taking the control member with it.
Figure 7:
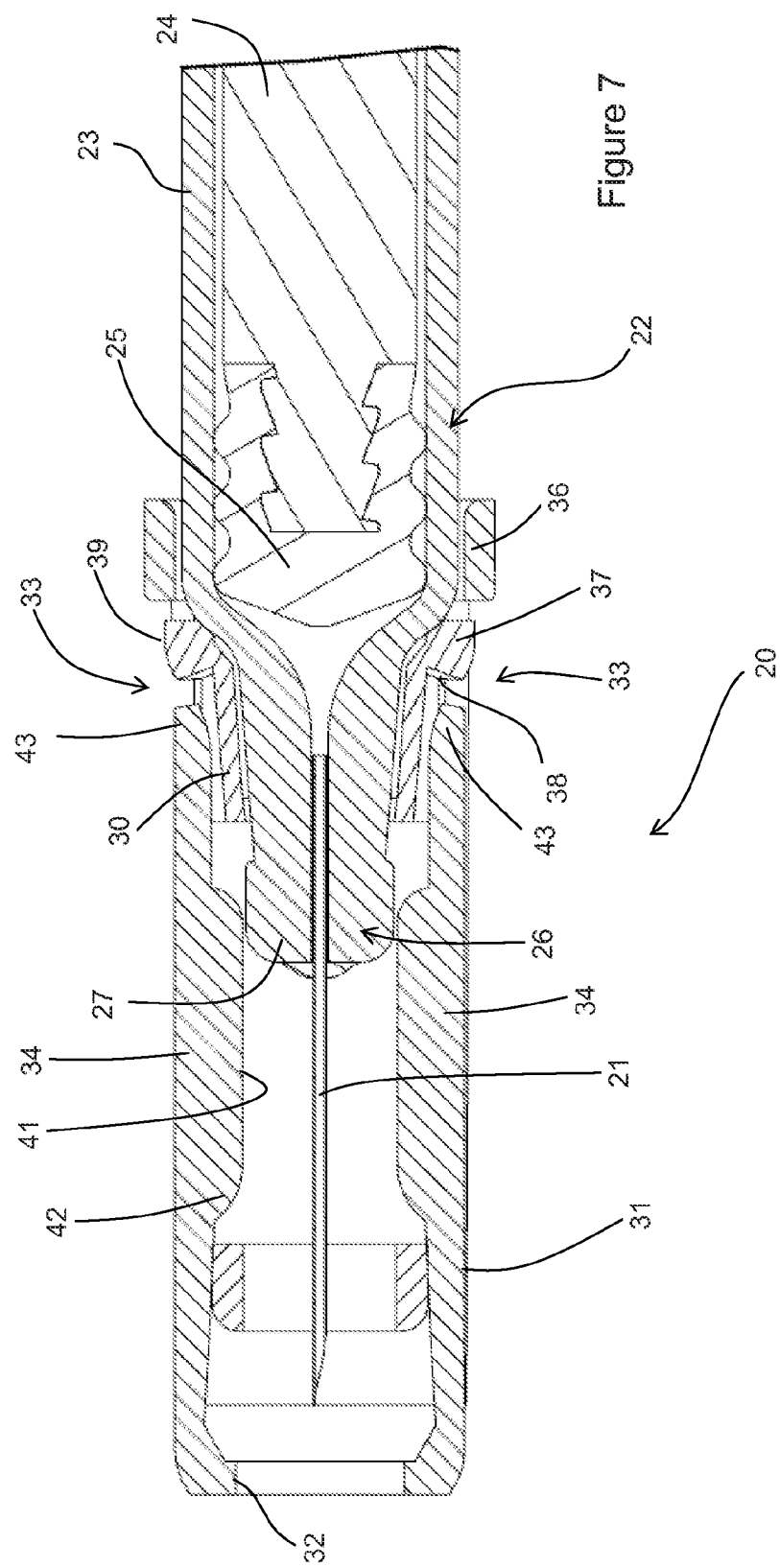
FIG. 7 shows the sleeve returned to and blocked in a needle shielding position.

The before-use needle shielding position of the sleeve is shown in FIGS. 1A and 1B, and the sleeve may slide rearwardly to a non-shielding position shown in FIG. 5, whereat most of the length of the needle back from its sharp tip 28 is exposed beyond the sleeve, so allowing a medical procedure to be performed. The sliding movement aforesaid of the sleeve may take place as a part of that procedure, such as performing an injection. Following completion of the procedure, the sleeve 31 may slide forwardly back to a shielding position, as shown in FIG. 7, and is then blocked in that position to prevent rearward sliding movement to expose the needle a second time.

The sleeve 31 has a pair of opposed elongate apertures 33 within which are formed respective fingers 34 attached to the main part of the sleeve at the forward ends 35 thereof, to serve as leaf springs. Though two such apertures each having a respective finger are shown, other numbers of apertures and fingers could be employed, ranging from a single aperture and finger up to three or four apertures and fingers and perhaps even five or more. Each finger 34 can be flexed resiliently, as will be apparent from the following description of the device.

Rearwardly of the fingers 34, the sleeve has an annular section 36 which is a free sliding fit on the body 23 of the syringe 22. The needle mount 30 has a pair of projecting lugs 37 which are located in the apertures 33. Relative rotation between the needle mount and the sleeve is thereby limited and movement of the sleeve further forwardly than is shown in FIGS. 1A and 1B is prevented by the annular section 36 abutting the lugs 37. Each of the lugs defines a forwardly facing abutment surface 38 and a sliding surface 39 for a purpose to be described below.

The inwardly facing inner surface of each finger 34 is provided with a camming surface 41. As shown in the drawings, the camming surface of each finger 34 extends for part of the length of the finger, and the ends of the camming surface are rounded as shown at 42, or the ends of the camming surface could be chamfered or profiled in any suitable way so as to provide a transition profile from the camming surface to the inner surface of the finger. The free end 43 of each finger can be chamfered, also as shown, for engagement with the abutment surface 38 of the needle mount, which abutment surface is similarly inclined to a true radial plane.

A generally annular control member 44 is supported within the sleeve 31 and, in the before-use position of the device as shown in FIG. 1B, is located on the enlargement 27 of the syringe nose, abutting the needle mount 30, the control member being freely slidable with respect to the needle mount. The junction between the circumferential outer surface 45 of the control member 44 and the forwardly directed radial face thereof may be rounded or chamfered, whereas the junction between that circumferential outer surface 45 and the rearwardly directed radial face of the control member is more angular; the function of these profiles will be described below. Moreover, the control member may not be strictly annular in shape but may have two diametrically opposed relieved portions 46 (see in particular FIG. 8) within which the camming surfaces of the fingers move during use of the device. It should be noted that FIGS. 1 to 7 are cross-sections through those relieved portions 46 and thus show the outer surface of the control member on which the camming surfaces of the fingers slide, in use of the device.

The operation of the safety device will now be described. The initial setting and position of the components described above is shown in FIGS. 1A and 1B. Here, the fingers 34 are shown in their relaxed condition in effect with their outer surfaces more or less parallel to the outer surface of the sleeve in the vicinity of the fingers. The rounded rearward ends of the finger camming surfaces 41 are adjacent the rounded forward profile of the control member 44, and the control member 44 abuts the needle mount 30. The sleeve 31 is prevented from moving forwardly from the position shown by virtue of the engagement of the annular section 36 of the sleeve with the needle mount lugs 37.

Figure 2:
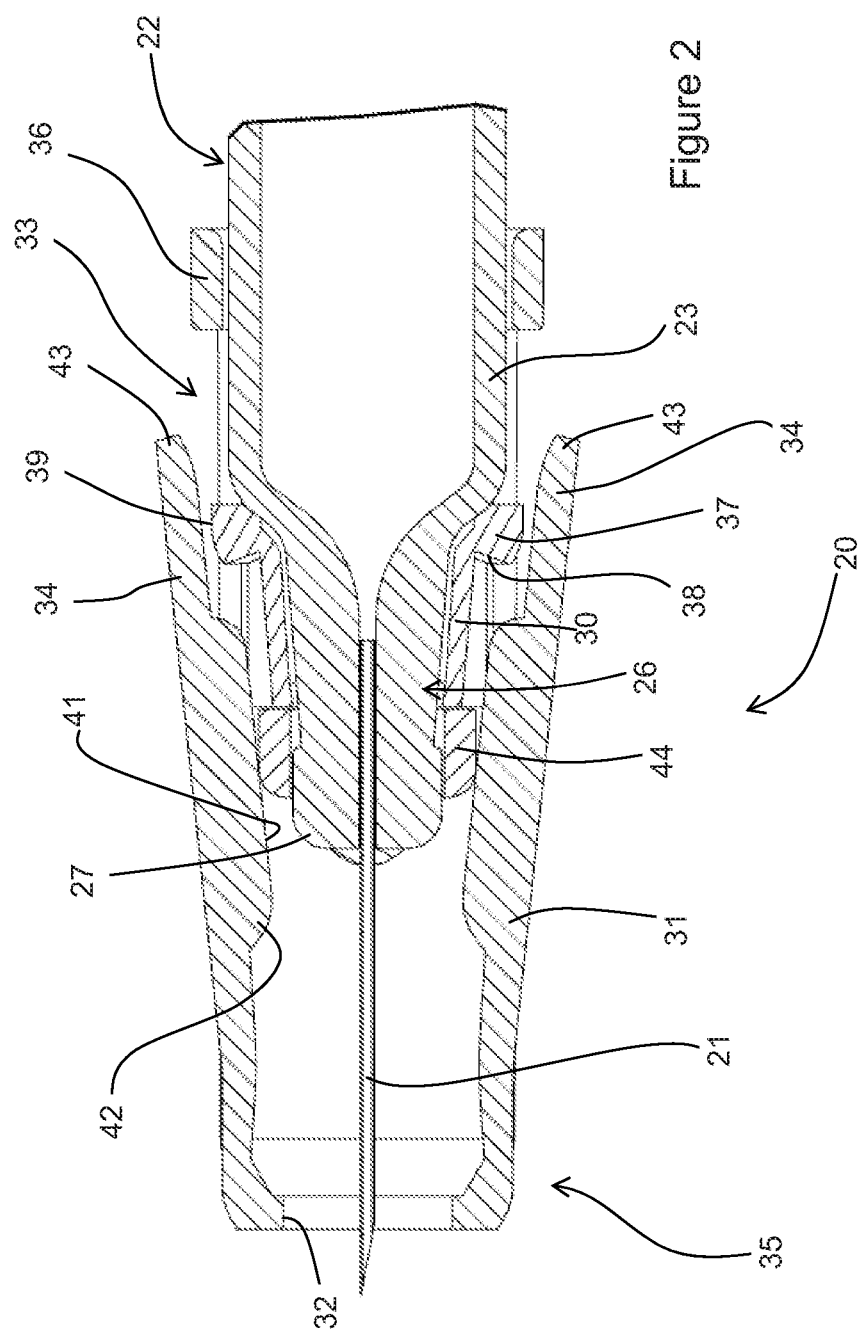
FIG. 2 is an axial cross-section through the safety device of FIG. 1B and showing the initial operation of the device with the sleeve moved from an initial setting.

From an initial position, the sleeve may be moved rearwardly relative to the needle 21 and syringe 22 by the application of a force to the sleeve but in use of the device this may occur by presenting the forward end 32 of the sleeve to the skin of a patient and pushing the syringe forwardly relative to the sleeve and patient, such that the needle penetrates the patient's skin. In the initial stage of sleeve movement as shown in FIG. 2, the camming surfaces 41 of the fingers bear and slide on the outer surface of the control member such that the free ends 43 of the fingers are moved outwardly, clear of the lugs 37. This flexing outwardly of the resilient fingers starts to store energy in those fingers.

Figure 3:
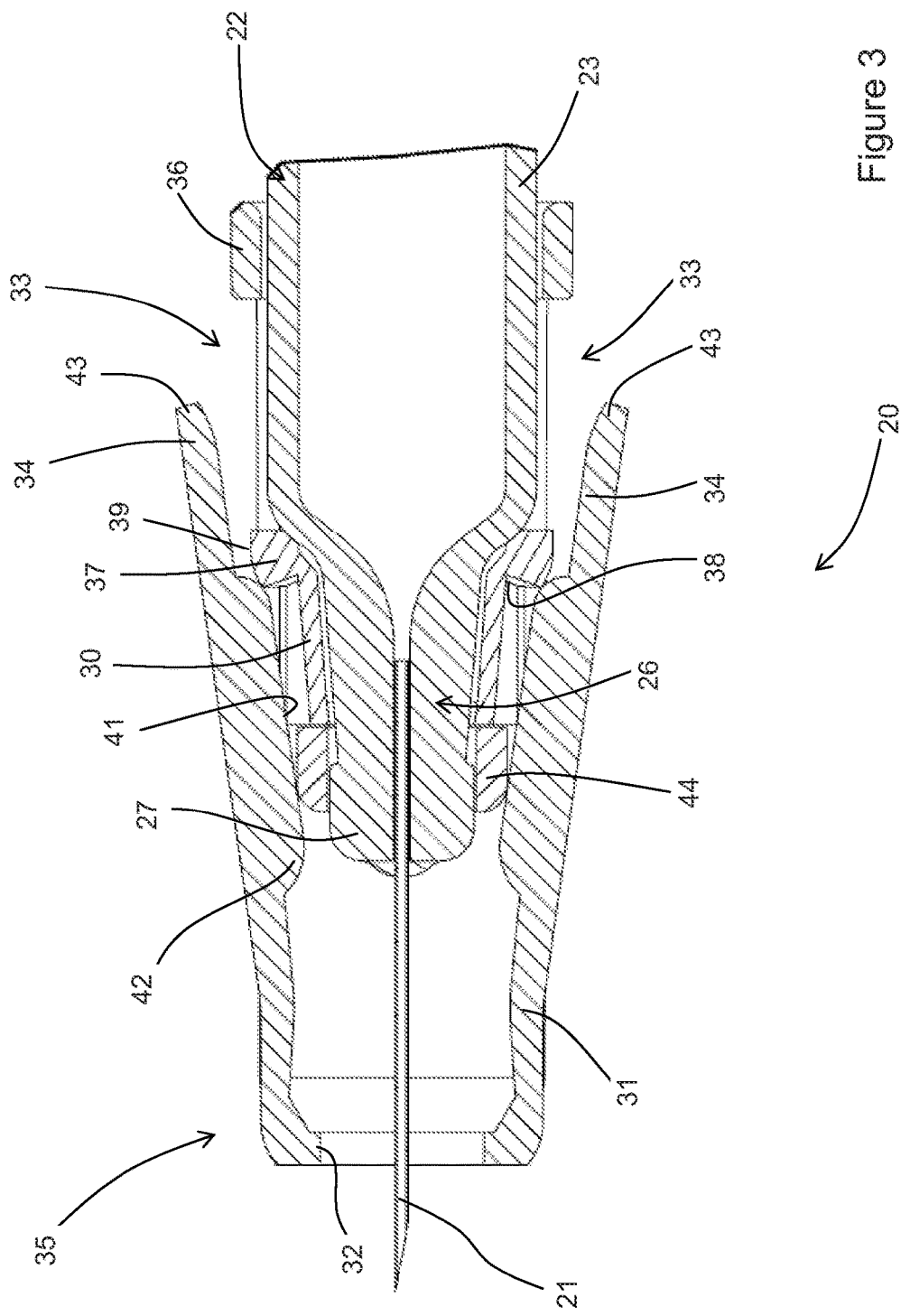
FIGS. 3 to 5 are similar to FIG. 2 but showing movement of the sleeve from the position of FIG. 2 sequentially to the sleeve being moved fully to a non-shielding position (FIG. 5)
Figure 4:
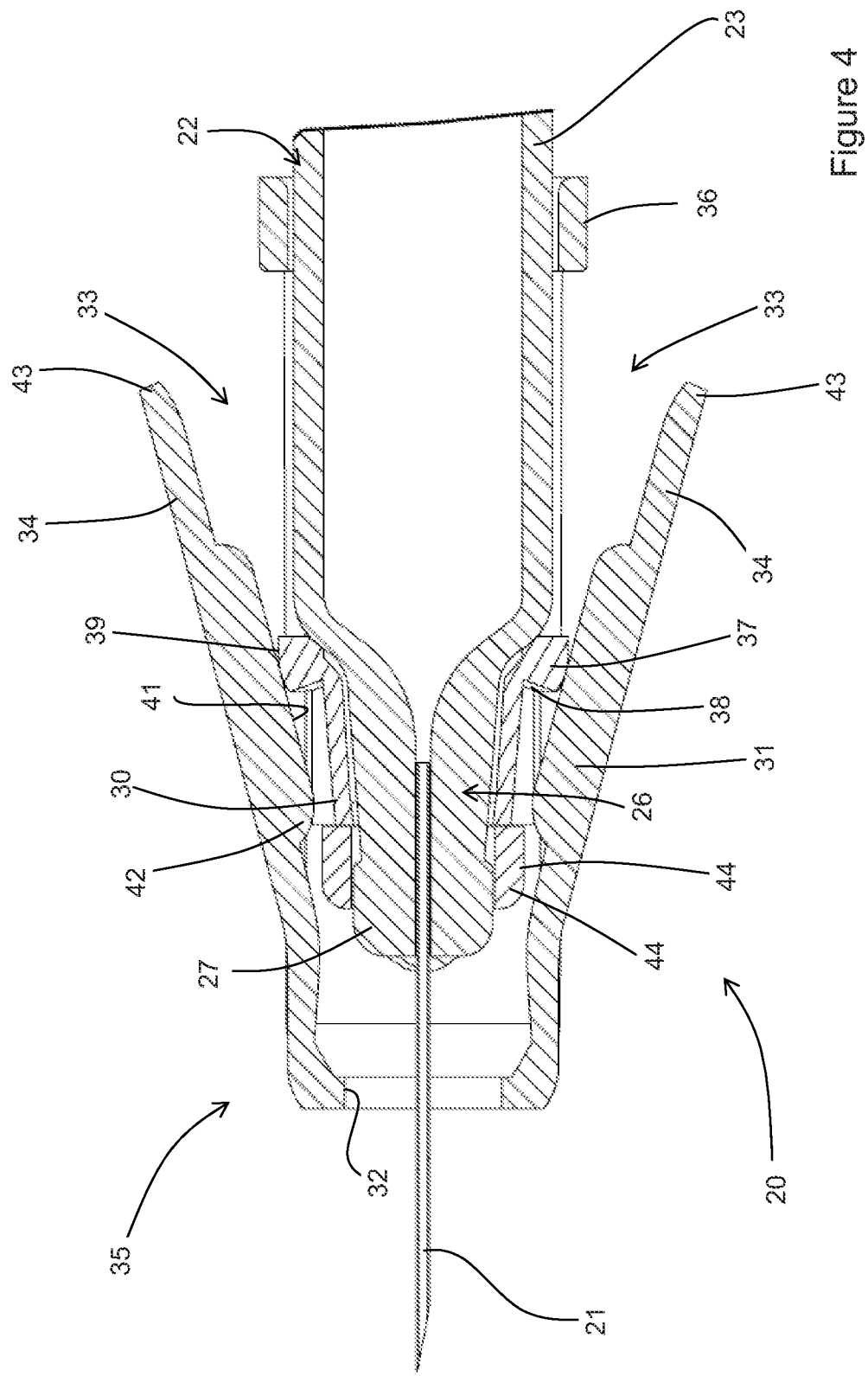

Continued rearward movement of the sleeve from this position where the needle projects from the end of the sleeve slides the camming surfaces along the outer surface of the control member and further deforms the fingers outwardly to increase the energy stored therein. Eventually, the rearward ends of the finger camming surfaces 41 come into sliding contact with the sliding surfaces 39 of the lugs 37 (FIG. 3). Further rearward movement of the sleeve then transfers the finger camming surfaces 41 on to the lug sliding surfaces 39 (FIG. 4) causing further resilient deformation of the fingers. The fully retracted position of the sleeve relative to the needle is shown in FIG. 5. Here, the deformation of the fingers is greatest and the internal bore at the forward end of the sleeve slides on to the control member 44, to be lightly frictionally engaged therewith. The control member does not play any further part in the operation of the device once the position of FIG. 5 has been reached. The injection may then be performed by pressing the plunger 24 forwardly, taking the piston 25 to the forward end of the body 23, as shown.

Following completion of the injection, the syringe and needle are pulled away from the patient so relieving the force on the sleeve 31. The stored energy in the finger acts through the camming surfaces 41 of the flexed resilient finger bearing on the sliding surface of the lug 37 to urge the sleeve forwardly (FIG. 6) so that the sleeve remains in contact with the patient's skin, as the syringe is moved away from the patient. The sleeve 31 carries with it the control member 44.

The final position is shown in FIG. 7. Here, the fingers 34 are no longer flexed and are back in their relaxed condition with their outer surfaces substantially aligned with the remainder of the sleeve. The free ends 43 of the fingers are in alignment with the abutment surfaces 38 of the lugs 37 and the control member 44 is frictionally engaged and disposed within the forward end of the sleeve 31, which surrounds the sharp tip of the needle. If now an attempt is made to move the sleeve rearwardly, the ends 43 of the fingers will engage the abutment surfaces 38 and block rearward movement of the sleeve. As mentioned above, by having the ends 43 chamfered and the abutment surfaces correspondingly profiled, inward deflection of the ends of the fingers is encouraged and thus assists retention of the interengagement of the finger ends and the abutment surfaces.

Figure 8:
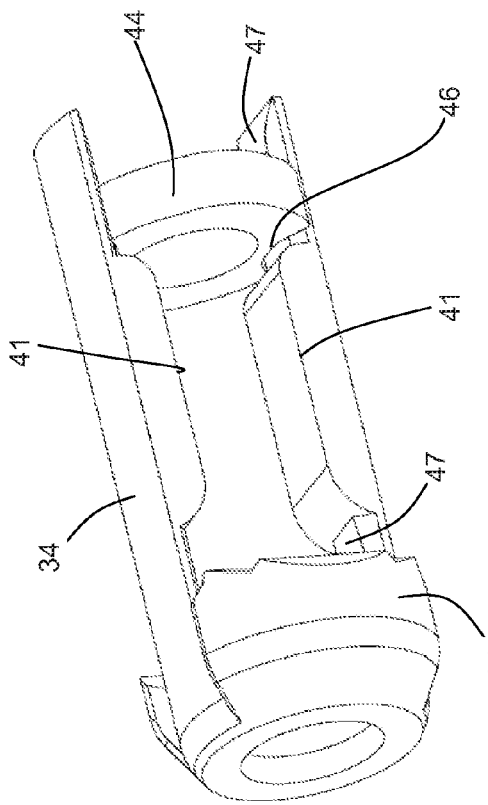
FIG. 8 is an isometric view of the sleeve and control member with other components cut away for clarity.

In an alternative arrangement for the inner surface of each finger, there is a pair of camming surfaces arranged side-by-side but spaced apart and there is a finger running surface on the inner surface of the finger and disposed between the camming surfaces. By an appropriate configuration of all of the finger camming surfaces, finger running surface, the control member outer surface and the lug sliding surface, the camming surfaces may run exclusively on the outer surface of the control member until the running surface comes into contact with and slides on the lug sliding surface but not on the control member. FIG. 8 shows such a configuration; the control member has opposed relieved portions 46 and on each side of the control member, the respective running surface 47 is located in a relieved portion until the camming surfaces 41 interact with the control member to each side of the relieved portion 46 to lift the end of the finger.

Also as shown in FIG. 8, the running surface extends along the finger to a greater extent than the camming surfaces but where the running surface lies between the two camming surfaces, the running surface may have a greater or lesser height than the two camming surfaces, or the three surfaces may be co-planar so as to define a single surface as shown in FIG. 8, upstanding from the inner surface of the finger.

In this arrangement there are two parallel and similar camming surfaces on the finger and the running surface is disposed between the camming surfaces, for at least part of the length of the running surface. In the alternative, there could be two parallel and similar running surfaces on the finger, with the camming surface disposed between the running surfaces for at least part of the length of the camming surface.

Figure 9:
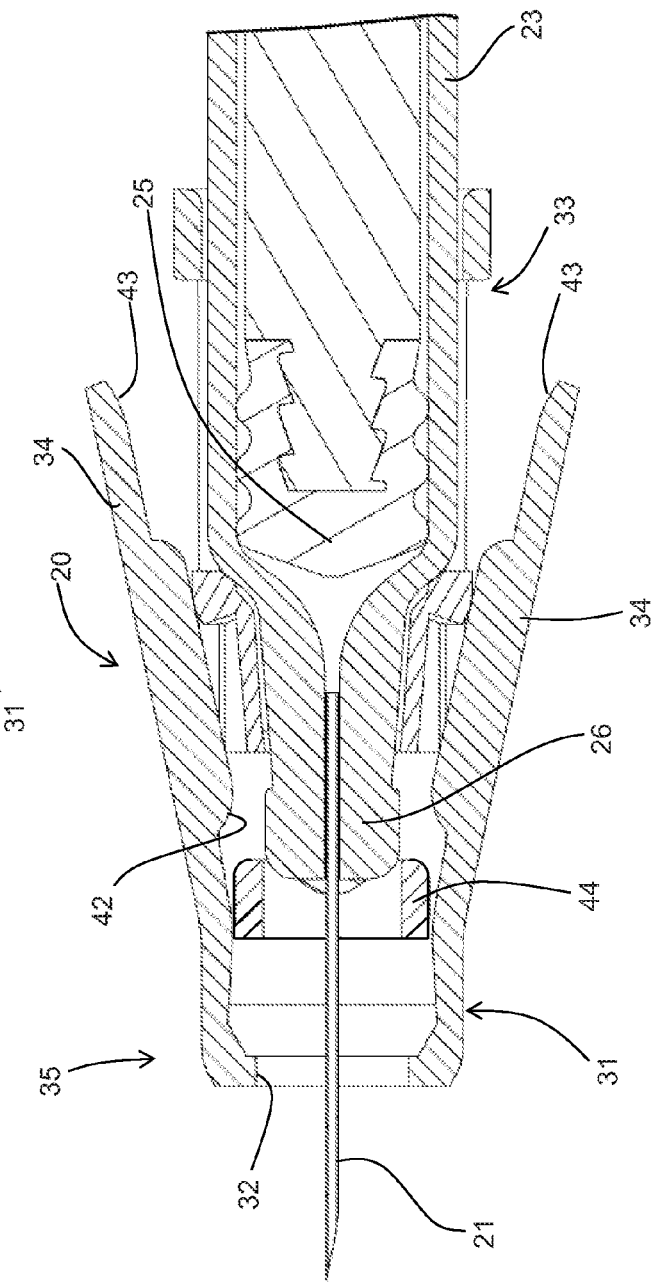
FIG. 9 corresponds to FIG. 3 but shows an alternative disposition for the control member.

FIG. 9 shows an alternative arrangement for the control member 44. In this, the control member has a relatively angular profile at the junction between the outer surface and the forwardly directed face thereof, in order to vary the way in which the profiles of the control member and camming surfaces interact. This angular profile can provide different frictional characteristics with the camming surfaces 41 of the fingers as compared to the embodiment described above, and in turn this changes the operational characteristics of the device. With this embodiment, there may be only low friction between the angular profile and the fingers and in turn this may cause the sleeve 31 to be urged forwardly after a relatively small rearward displacement of the sleeve.

Either arrangements of this invention as described above may have the operational characteristics tuned by changing one or more of (a) the profile of the surface of the control member engaged by the camming surfaces of the fingers, (b) the profile of the camming surfaces themselves, and (c) the profile of the sliding surfaces of the lugs 37 engaged by the camming surfaces. For example, the camming surfaces 41 may taper gradually to be of reducing height in a direction away from the finger end 43. Further, the profile of the junction between the external surface of the control member and the forwardly directed face thereof may be made more or less rounded or angular, and equally the profile of the lug sliding surface 39 may be similarly altered to give the required characteristics to the movement of the sleeve under the action of the spring force of the fingers. Yet further possibilities are to adjust the surface finish of the interengaging components or of the materials from which the components are made, thereby to control the operational characteristics of the device.

In the above ways, the sleeve may be maintained in an intermediate position following displacement from its initial shielding position or the sleeve can be immediately urged forwardly by the fingers. In the former case, the length of needle back from the sharp tip which is exposed in the intermediate position may be controlled and predetermined during the manufacture of the device. In all these cases, following the transfer of the finger camming surfaces to the lug sliding surfaces should be arranged to ensure that thereafter, the fingers will urge the sleeve forwardly to a shielding position, due to the contact of the finger with the sliding surface of the lug, which will result in the finger acting to urge the sleeve to a needle shielding position.

With the above described embodiment of this invention the device presents a relatively large diameter bore extending therethrough, within which is, or is to be, located the needle. In view of the large diameter, a collision between the tip of the needle and the bore during assembly of the needle to the device is much less likely than with many known safety devices, so greatly minimising the likelihood of damage to the tip of the needle.

FIGS. 10 to 18 show a second embodiment of safety device of this invention. This embodiment has a square cross-sectional tubular shape, unlike the first embodiment, but functionally is similar to the first embodiment.

In FIGS. 10 and 11 there is shown a syringe 50 which is essentially the same as that described above with reference to FIGS. 1 to 7. Thus, the syringe has a body 51 provided with a flange 52 at its rearward end, a plunger 53 extending into the syringe body for expelling drug from the body through a needle 54 projecting forwardly from the nose cone 55 at the forward end of the syringe.

The safety device has a needle mount 57 snap-fitted on to the nose cone 55 of the syringe. The needle mount includes a pair of outwardly projecting lugs 59 (only one of which can be seen in FIG. 11) defining an abutment surface 60 extending in a plane normal to the axis of the device and a sliding surface 61 inclined to the axis of the device. Further, formed in the needle mount 57 is a pair of ramp surfaces 62 for a purpose to be described below.

A hollow sleeve 64, also of square cross-sectional shape, is slidably carried on the needle mount 57. The sleeve has a pair of opposed side faces 65 in each of which is an elongate aperture 66. In each aperture, there is a resilient flexible finger 67 (only one of which is visible in FIGS. 10 and 11) each finger being integral with the sleeve at its forward end and its rearward end being free to flex inwardly or outwardly relative to the sleeve, as in the previous embodiments described above. In its relaxed condition, the outer surface of the finger 67 is essentially co-planar or parallel with the side face of the sleeve within which that finger is provided. The inner surface of the finger has a profile which will be described in more detail below but which serves to flex the finger outwardly when the device is in use, so as to store energy in the finger.

When the sleeve is located on the needle mount 57 as shown in FIG. 10, the lugs 59 project into the respective apertures 66 at the rearward ends thereof. The interengagement between the lugs and the sleeve rearwardly thereof prevent the sleeve moving forwardly off the needle mount 57. In this condition, the rearward ends 68 of the fingers 67 lie closely adjacent the respective abutment surface 60 for a purpose again to be described below.

A control member 70 (FIG. 11) is disposed within the sleeve 64 for sliding movement with respect thereto. The control member has a central opening 71 which, in the initial setting of the device, receives the enlargement 58 of the needle mount 57 such that the rearward face of the control member abuts the needle mount 57. The control member has a generally planar front face 72 and two pairs of opposed planar side faces 73 and 74. The side faces 73 have a central slot 75 and the junction between those side faces 73 and the front face 72 is rounded, as shown in FIG. 11. The pair of side faces 74 are plain and slide on the corresponding plain side faces of the sleeve 64.

The sleeve 64 has a front face 77 with a hole 78 formed centrally therein, through which the needle 54 of the syringe projects when the sleeve 64 is moved rearwardly with respect to the syringe 50. The central hole is of a sufficient size to accommodate a hard or soft needle shield, as with the previous embodiment.

The internal profile of the inner surface 79 of each finger 67 can best be seen in FIGS. 19 and 20, to which reference will now be made. Disposed on the inner surface of the finger, along each side thereof is a pair of camming surfaces 80 with a running surface 81 disposed between those camming surfaces. In the configuration shown in FIG. 19, the running surface 81 is co-planar with the camming surfaces 80 and thus there appears to be a single planar surface though the camming and running surfaces can be distinguished by the function they perform. In the configuration of FIG. 20, the running surface 82 between the camming surfaces 80 upstands above the camming surfaces so that there appears to be a rib projecting above the camming surfaces. In yet another configuration (not shown) the running surface has a lesser height than the camming surfaces such that there appears to be a groove between the camming surfaces and in which the sliding surface of the lug is received so that the running surface may bear thereon.

Figure 21:
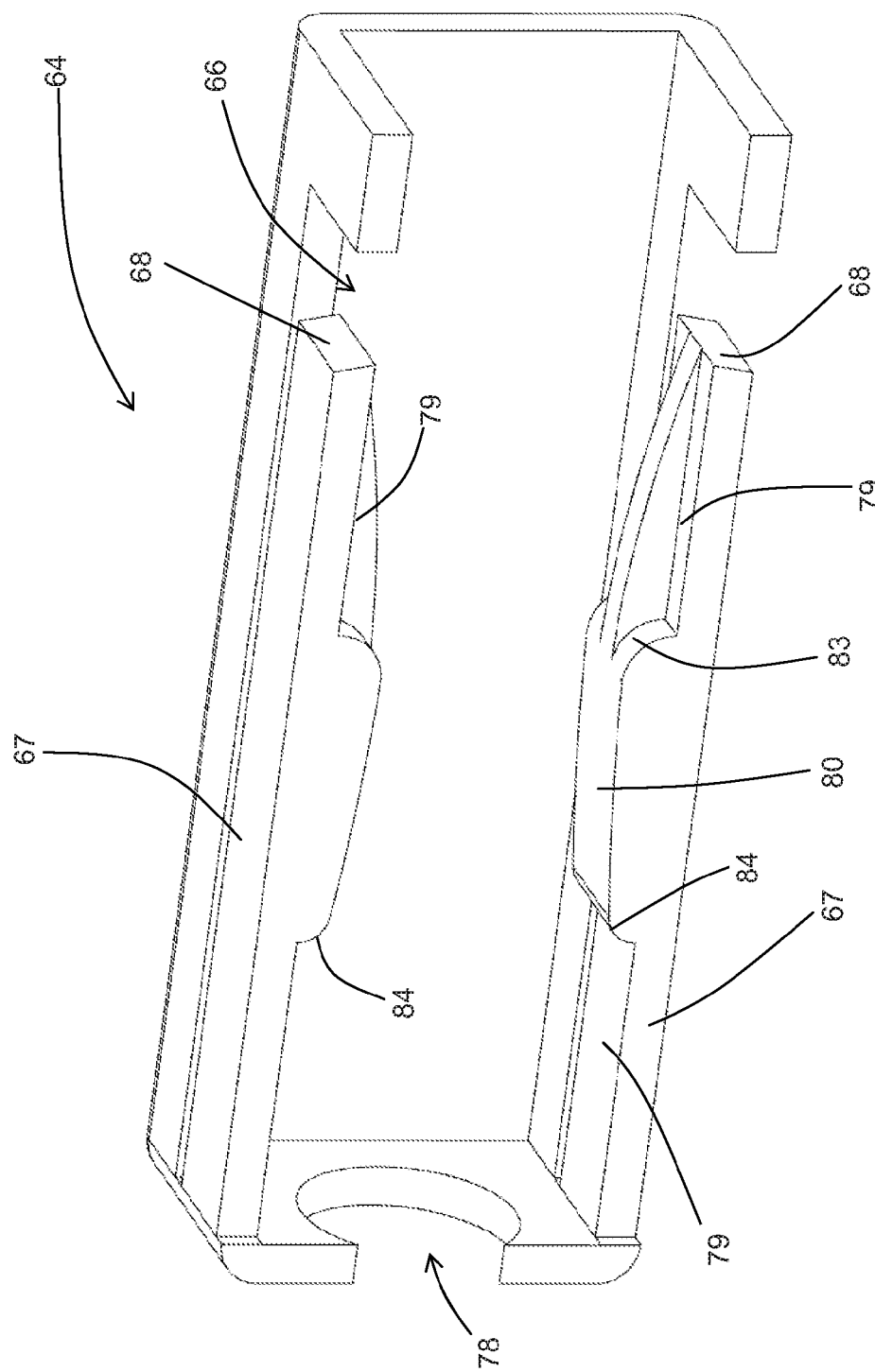
FIG. 21 shows a sleeve similar to that of FIG. 19 but with a shorter camming surface.

FIG. 21 shows a slightly different camming surface on each of the two fingers. Here, the camming surface is significantly shorter than as shown in FIGS. 19 and 20. In this case, the camming surface will run off the outer surface of the control member so that the inner surface of the finger will bear on the sliding surface of the lug, with a lesser sleeve movement. Thereafter, further rearward sleeve movement will result in the finger being flexed to a greater extent with more energy stored in the finger, by the interaction between the finger and the lug sliding surface.

The camming and running surfaces have a reducing height in the forward direction away from the finger end, as can be seen in the drawings and the forward ends 83 of those surfaces are rounded, down to the inner surface 79 of the finger. Similarly, the rearward ends 84 of the camming surfaces 80 are rounded but the running surface 81 (FIG. 19) or 82 (FIG. 20) is of gradually reducing height in the rearward direction. At the rearward end 68 of the finger, the height of the running surface is zero—that is to say, it is coincident with the inner surface 79 of the finger.

The initial setting of the components described above is shown in FIGS. 12A and 12B. Here, the needle mount 57 is snap-fitted to the syringe nose 55 and is prevented from coming off that nose by interengagement between the needle mount and the enlargement 58 of the nose. The control member 70 can be located on the enlargement 58 abutting the needle mount (as shown), with the rounded junction between its front face 72 and side faces 73 facing forwardly. The lugs 59 of the needle mount are received in the elongate apertures 66 of the sleeve 64 and so prevent the sleeve moving forwardly from the position shown. Here, the sleeve is fully protecting the sharp tip 85 of the needle 54 and the rounded rearward ends 84 of the camming surfaces lie closely adjacent the rounded profiles of the control member, though the running surfaces 81 of the fingers are disposed in the slots 75 and preferably do not contact the control member.

In order to perform a medical procedure such as an injection with the device described above, from an initial position as shown in FIGS. 12A and 12B, the front face 77 of the sleeve is offered to the skin of a patient at the required injection site and the syringe 50 is pushed forwardly with respect to the sleeve. In effect, therefore, the sleeve moves rearwardly with respect to the syringe, needle and needle mount and will be described as such, in the following.

Figures 13A, 13B:
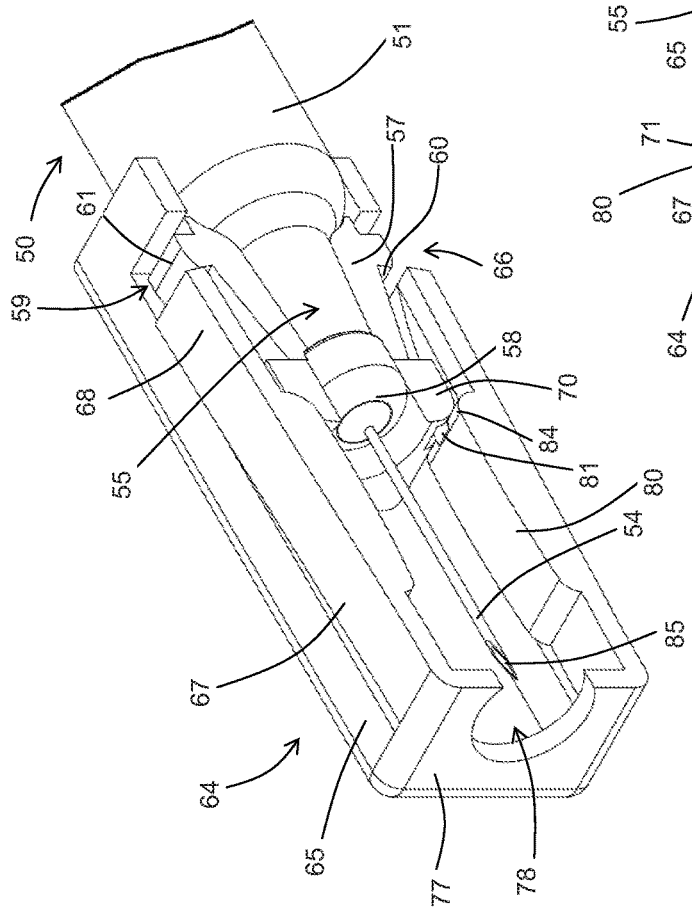

During initial movement of the sleeve from its protecting position shown in FIGS. 12A and 12B, the rounded rearward ends 84 of the camming surfaces 80 move up the rounded junction between the front face 72 and side faces 73 of the control member as shown in FIGS. 13A and 13B. The fingers are thus flexed outwardly and in view of the resilience of those fingers, energy is immediately stored in those fingers. This outward flexing of the fingers lifts the rearward ends 68 of the fingers out of alignment with the abutment surface and clear of the lugs 59 of the needle mount 57.

As the rearward ends 68 of the fingers are flexed clear of the abutment surface and the lugs 59, continued rearward movement of the sleeve is possible. This moves the camming surfaces 80 further along the outer side faces 73 of the control member (FIGS. 14A and 14B) increasing the flexing of the fingers and thus also increasing the energy stored therein. Yet further rearward movement of the sleeve 64 slides the camming surfaces along the control member until the position shown in FIGS. 15A and 15B is reached, where the rounded forward ends 83 of the camming surfaces are at the rearward end of the control member 70 but are still bearing exclusively on that control member and the deflection of the fingers is greatest with the maximum energy stored therein. It should be noted that the camming surfaces are here still clear of the sliding surfaces 61 of the lugs 59.

Further rearward movement of the sleeve takes the camming surfaces 80 off the control member such that, for each finger, the running surface 81 disposed between the camming surfaces 80, is brought to bear on the respective sliding surface 61 of the adjacent lug 59, causing the fingers to be moved towards the lugs 59. This is shown in FIGS. 16A and 16B.

Typically the medical procedure would be performed with the device in this setting and on completion, the syringe is moved away from a patient so as to withdraw the needle 54. During this rearward movement of the syringe, the sleeve is urged forwardly and driven with respect to the syringe by the energy stored in the fingers, the running surfaces 81 of the fingers interacting with the lug sliding surfaces 61 (FIGS. 17A and 17B) to generate a spring force acting to urge the sleeve forwardly to a needle shielding position. During this action, the control member 70 remains in the forward part of the sleeve with the rounded forward ends 83 of the camming surfaces acting on the outer surface of the control member to hold the control member in a forward part of the sleeve. Alternatively, or perhaps in addition, there could be light frictional contact between the outer surface of the control member and a forward part of the sleeve to retain the control member in that forward part.

Figure 18A:
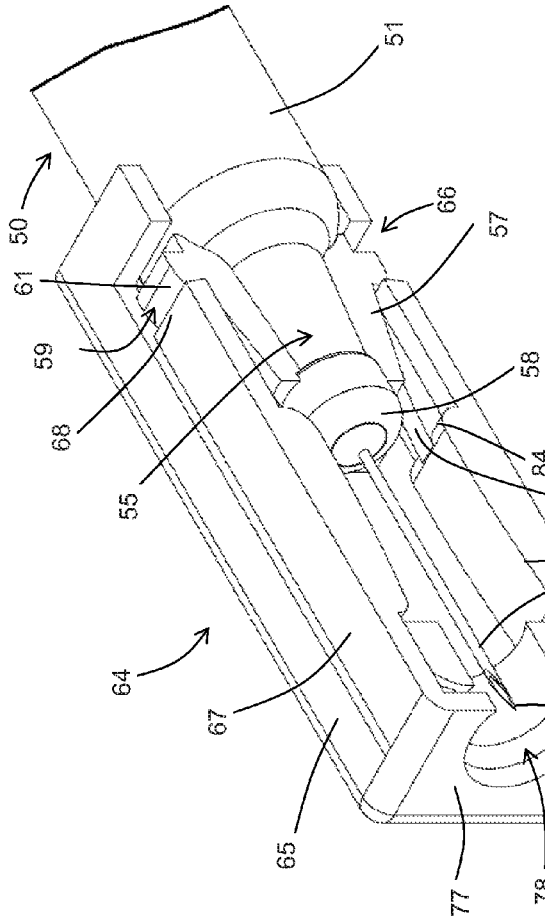
Figure 18B:
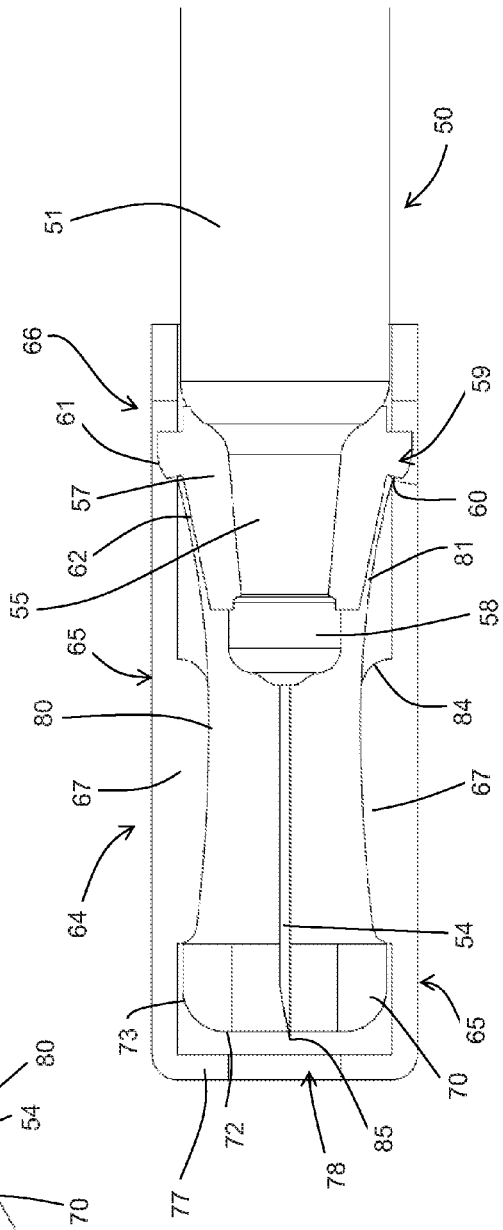

As the syringe is pulled away from the patient, the sleeve remains in contact with the patient whilst the needle is fully withdrawn as shown in FIGS. 18A and 18B and the sleeve is protecting the sharp tip of the needle, the control member still being present in the forward part of the sleeve. The fingers are no longer flexed and return to their relaxed condition and the rearward ends 68 of the fingers are located immediately adjacent the abutment surfaces 60 of the needle mount. Any attempt to move the sleeve rearwardly will be blocked by the inter-engagement of the rearward ends of those fingers with the abutment surfaces and those surfaces can be profiled as shown such that an increasing force applied to the sleeve will enhance the blocking effect of the fingers engaged with the abutment surfaces.

Though not shown, it would be possible to provide a window in the sleeve 64 at its forward end, in order that the presence of the control member at the forward end of the sleeve may be observed to give an indication that the safety device has been used and that the sleeve is blocked in its protecting position shown in FIGS. 18A and 18B. By having a highly coloured control member the fact that the condition of FIGS. 18A and 18B has been reached will be more obvious.

FIGS. 22A, 22B, 23A and 23B show a third embodiment of safety device of this invention, similar to that of FIGS. 10 to 18 but the control member 87 has a different profile as compared to the control member of the second embodiment and the camming surfaces 88 of the fingers 89 are provided with a detent 90 to receive the control member. In this embodiment, the two opposed outer surfaces of the control member which are contacted by the camming surfaces of the fingers are rounded, as shown in the drawings. In all other respects, the control member 87 corresponds to control member 70 of the second embodiment and thus the control member includes a central opening 71 and a slot 75 for the running surface 81 of the fingers. The detent 90 in each finger is rounded with essentially the same radius of curvature as the outer surface of the control member such that the control member will be received snugly in those detents.

In an initial setting of the third embodiment, and during a first stage of movement, corresponds to that of the second embodiment. FIGS. 22A and 22B show this third embodiment partway through operation, where the sleeve 64 has been moved rearwardly, initially to lift the rear ends of the fingers 89 clear of the abutment surfaces 60 and then to continue the resilient flexing of the fingers, until the control member 87 is received in the detents 90. The sleeve of the device may remain in this setting indefinitely, even if all rearward pressure is removed from the sleeve 64, as the control member 87 is held by the detents 90 in the camming surfaces 88. The sleeve may be set to this position manually, or by means of a container for the safety device, from which the device is removed before use, such as has been described in EP 2203202 (Liversidge).

From the position of FIGS. 22A and 22B, the sleeve may be moved further rearwardly to the position shown in FIGS. 23A and 23B. Here, the detents 90 have not reached the sliding surfaces of the lugs 59 and therefore the sleeve 64 is not held in this position. Rather, the spring force provided by the flexed fingers urges the sleeve forwardly. The operation from the position of FIGS. 22A and 22B to that of FIGS. 23A and 23B, and back to the initial shielding position is exactly as has been described above with reference to FIGS. 10 to 18. The control member 87 is located in the forward part of the sleeve 64 such that the control member will remain static relative to the sleeve when the sleeve moves forwardly, under the spring force provided by the fingers 89, with each running surface 81 thereof acting on the respective sliding surface of the lugs 59. As mentioned above, the control member may additionally or alternatively be frictionally engaged with a forward part of the sleeve.

Figure 22:
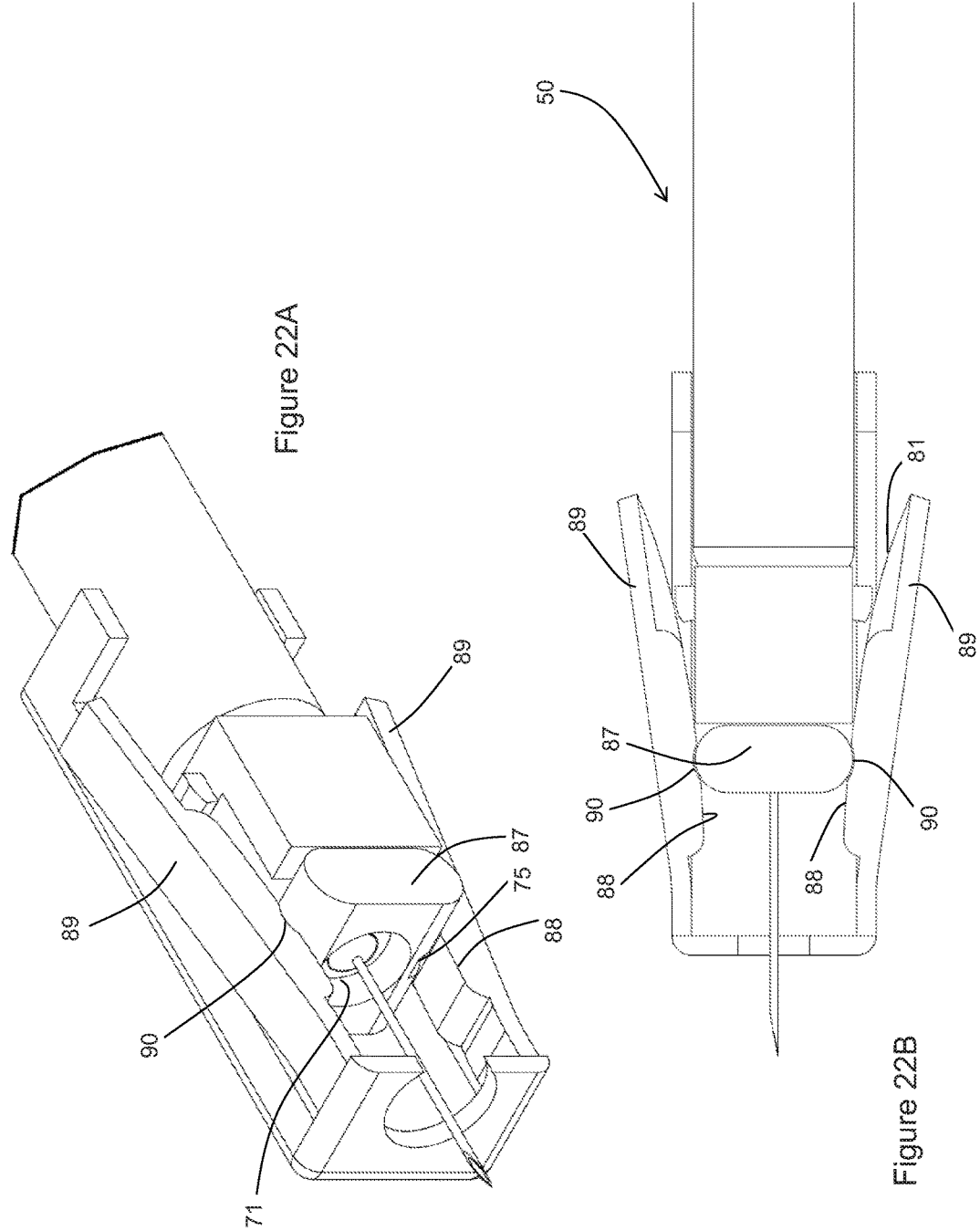
FIGS. 22A and 22B are isometric and axial sections of a third embodiment including a detent arrangement, part-way through the movement of the sleeve rearwardly from a shielding position.
Figure 23:
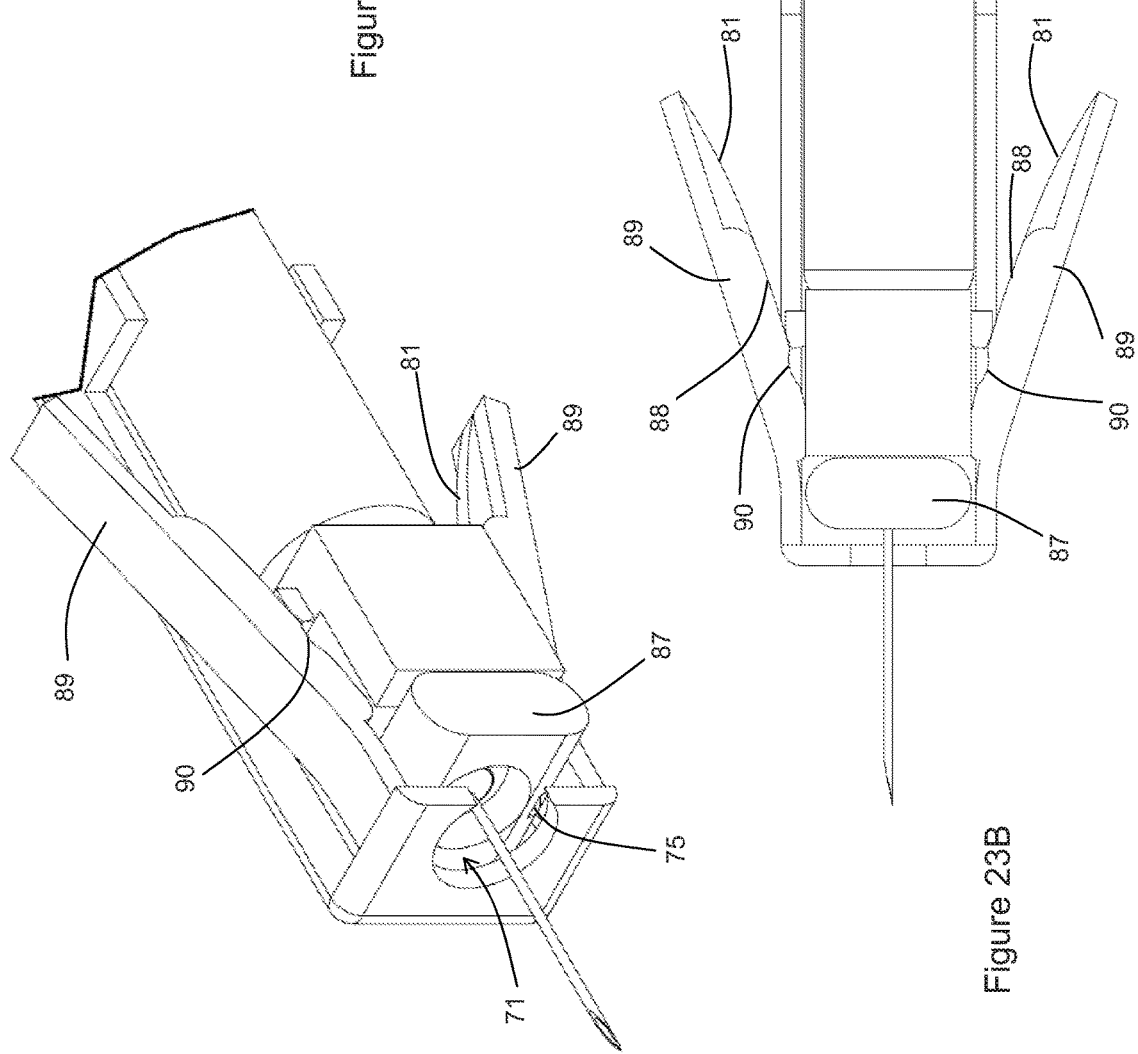
FIGS. 23A and 23B show the third embodiment, with the sleeved moved fully rearwardly.

The third embodiment shown in FIGS. 22 and 23 can be modified so that the camming surface of each finger has a protrusion partway therealong, which protrusion is receivable in a correspondingly-profiled recess in the outer surface of the control member. In this way, the same functionality can be obtained with this modified form of the third embodiment as is obtained with the third embodiment itself, described with reference to FIGS. 22 and 23.

Figure 24:
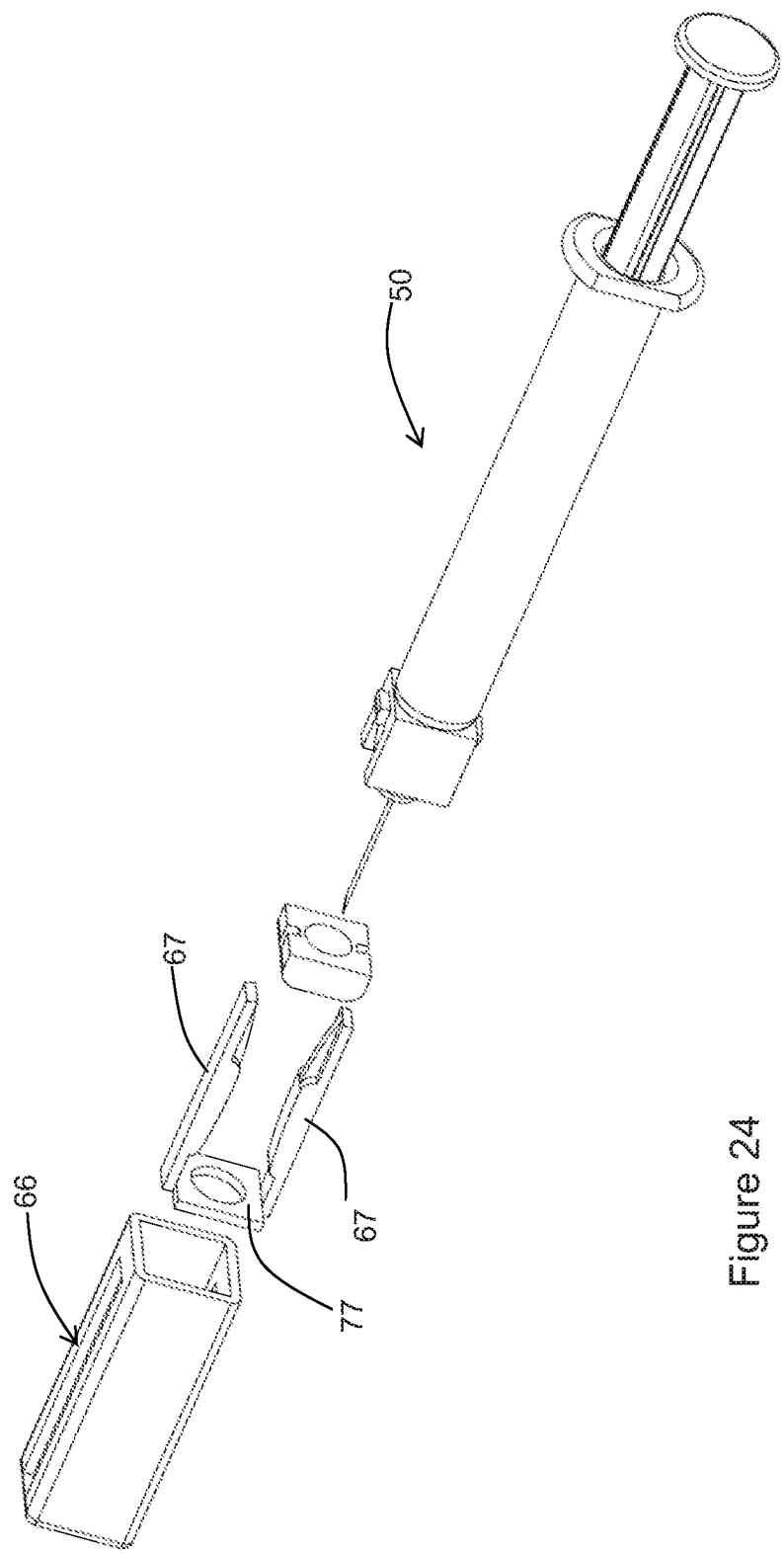
FIG. 24 shows an alternative construction for the sleeve and fingers, as compared to the second embodiment of FIGS. 10 and 11.

FIG. 24 shows an arrangement of sleeve similar to that described above with reference to FIGS. 10 to 20 but differs in that the fingers 67 are provided as a separate unit together with the front face 77 of the sleeve. The sleeve itself is thus a simple moulding of square cross-sectional shape but having the elongate apertures 66 in two opposed side faces. Equally, the unit of the fingers and front face is relatively simple to mould and may be snap-fitted into the sleeve. In all other respects, the arrangement of FIG. 21 corresponds to that described above.

Figure 25:
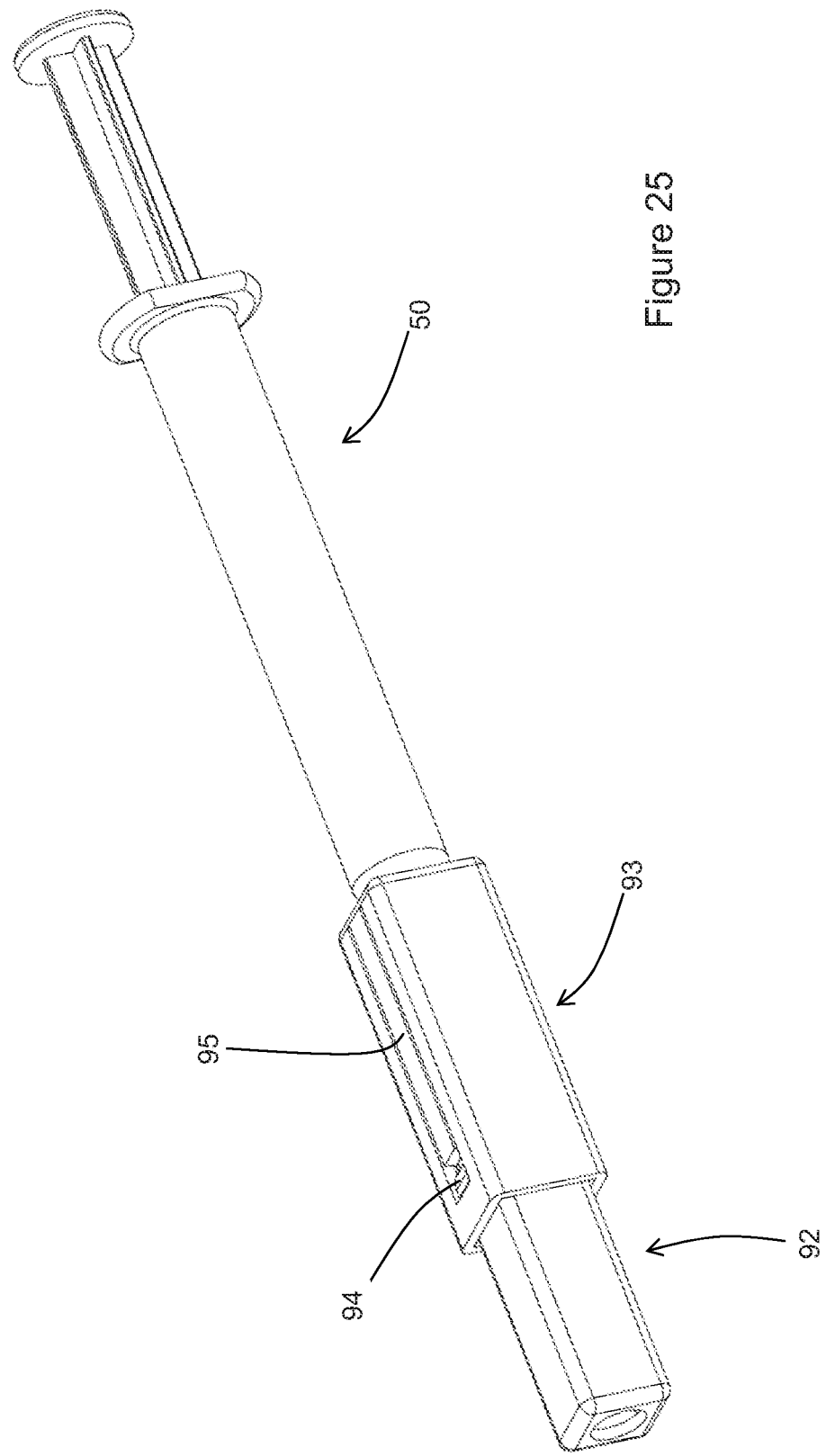
FIG. 25 is an isometric view of a syringe carrying a fourth embodiment of safety device.

FIG. 25 shows a fourth embodiment which operates on exactly the same principles as described above with reference to the second embodiment of FIGS. 10 to 18 but here the sleeve 92 slides internally within the needle mount 93. The sleeve has lugs 94 performing exactly the same function as the lugs 59 of the second embodiment and the fingers 95 project forwardly from the rear end of the needle mount 93, for co-operation with the lugs 94 to block rearward movement of the sleeve 92, when the device has been used.

Internally, the arrangement is the same as that of the second embodiment and thus there is a control member (not shown) which performs the same function in the same way as has been described above. Thus, the control member flexes the fingers outwardly during initial rearward movement of the sleeve such that the fingers store energy and also are lifted clear of the abutment surfaces of the lugs 94. Continued rearward movement of the sleeve 92 increases the resilient flexing of the fingers 95 and when the sleeve has been moved fully rearwardly, the energy stored in the fingers serves to drive the sleeve forwardly when the syringe is moved away from a patient. Finally, blocking of the sleeve in its protecting position is achieved in exactly the same way as with the second embodiment.

Figure 26:
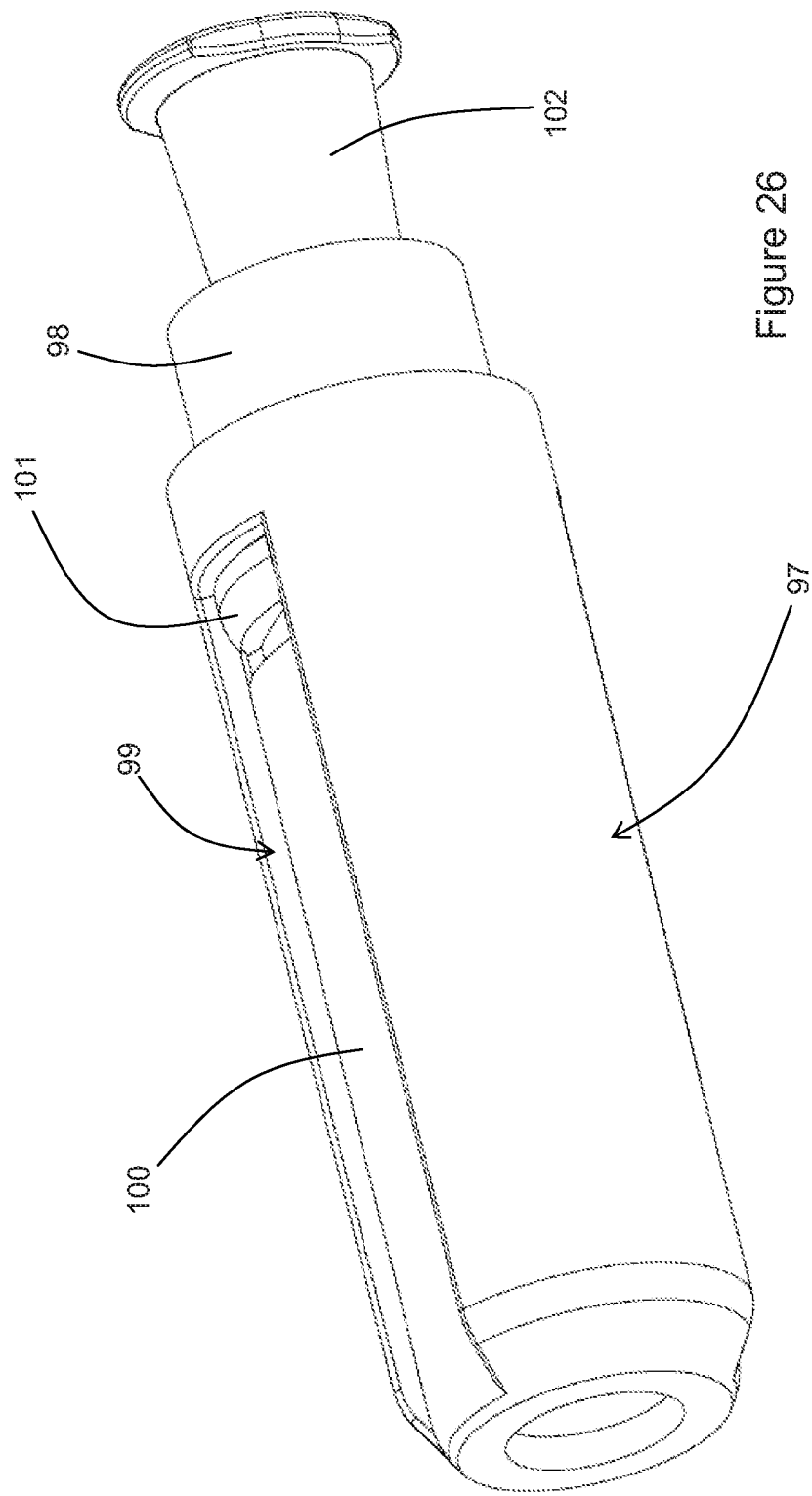
FIG. 26 shows a fifth embodiment of safety device corresponding to that of FIGS. 1 to 9 but having a Luer slip connection for connection to a conventional syringe.

FIG. 26 shows a fifth embodiment of safety device of this invention. This fifth embodiment has a sleeve 97 slidably mounted on a needle mount 98, the sleeve having a pair of opposed apertures 99 (only one of which is visible in FIG. 26) with a respective resiliently flexible finger 100 located in the aperture. The needle mount 98 has a pair of lugs 101 located in the apertures 99 and carries a needle projecting forwardly within the sleeve 97. The internal arrangement of this fifth embodiment (including a control member) corresponds to that of the first embodiment and has exactly the same functionality. The needle mount has a Luer taper socket 102 for connection to a Luer spigot at the forward end of a conventional syringe, whereby the safety device may be connected to that syringe when an injection is to be performed.

Figure 27:
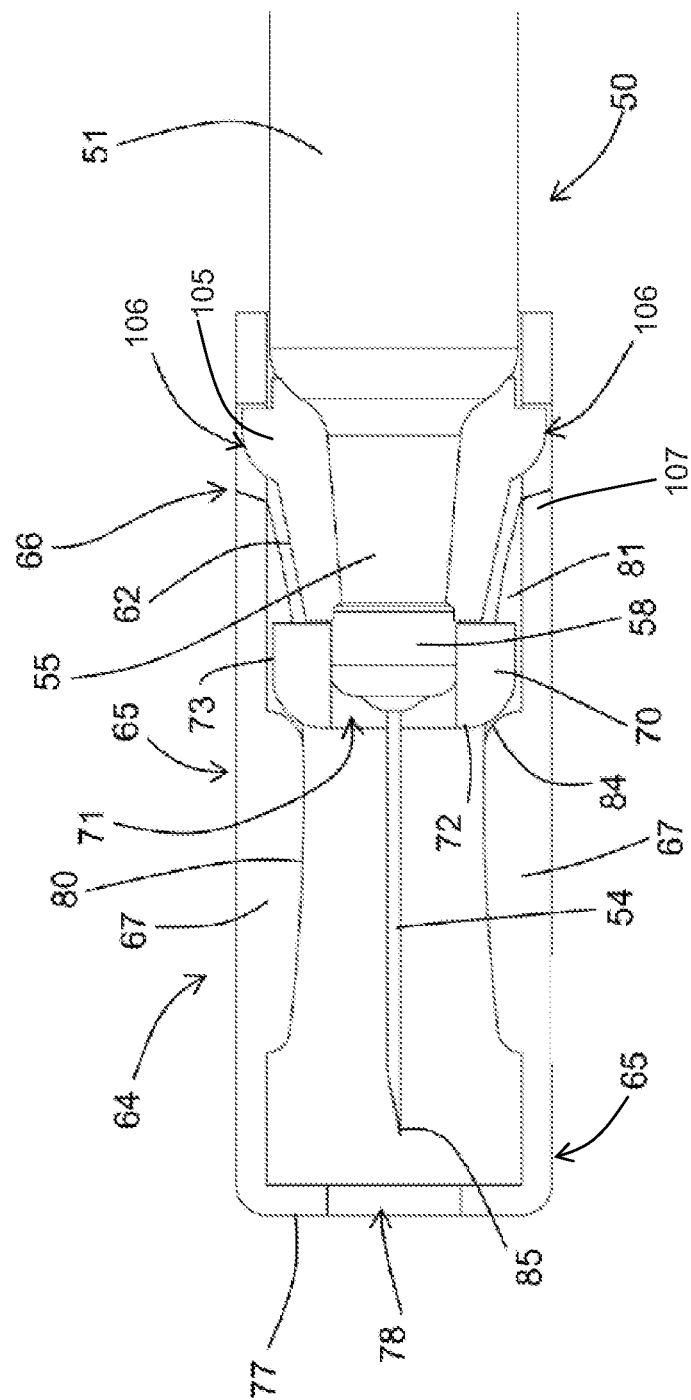
FIG. 27 shows a sixth embodiment of safety device wherein no locking of the sleeve in its needle shielding position takes place, following use of the device.

A sixth embodiment of safety device of this invention is shown in FIG. 27 and like parts with those of FIG. 12 are given the same reference numerals. The sixth embodiment differs from the second embodiment (exemplified by FIG. 12) in that the sleeve is not blocked against rearward movement following use of the device and the return of the sleeve to its before-use needle shielding position. As a consequence, the sleeve may be moved rearwardly from a needle shielding position more than once but after the first time, the control member will not participate in lifting the fingers in the manner described above with reference to FIG. 12.

The sixth embodiment has lugs 105 which do not present an abutment face but rather are rounded as shown at 106 in FIG. 27, and the rearward ends 107 of the fingers are chamfered, again as shown. The consequence of this is that following use of the device and the return of the sleeve 64 to its needle protecting position, the sleeve may be moved rearwardly for a second time with the fingers 67 being lifted by virtue of the interaction of the chamfered ends 107 of the fingers with the rounded surfaces 106 of the lugs 105. As the control member 70 will be in a forward part of the sleeve 64, energy will be stored in the fingers by direct interaction between the inner surfaces of those fingers and the lugs 105.

The invention claimed is:

1. A safety device for shielding a medical needle having a sharp tip, comprising:
   a needle mount for directly or indirectly supporting the safety device with respect to the medical needle;
   a needle shielding sleeve for surrounding the needle and arranged coaxially with the mount for sliding rearward movement relative to the mount from a needle shielding position towards a non-shielding position whereat at least the tip of the needle is exposed beyond the sleeve;
   a sliding surface provided on one of the sleeve and mount;
   at least one elongate resiliently flexible finger provided on the other of the sleeve and mount and serving as a spring to return the sleeve to a needle shielding position, the finger having an inner surface; and
   a control member having an outer surface and arranged coaxially with the sleeve and mount, the control member having an initial set position with respect to the finger and being slidably displaceable with respect to the finger from said set position when the sleeve slides towards the non- shielding position;
   wherein the inner surface of the finger is provided with an elongate camming surface and there being a transition profile between the camming surface and the inner surface; such that:
   rearward movement of the sleeve to the non-shielding position displaces the control member from its initial set position with respect to the finger so that the outer surface of the control member interacts with the camming surface of the finger, thereby flexing the finger to generate and store energy therein for returning the sleeve to a needle shielding position;
   and thereafter further rearward movement of the sleeve further displaces the control member so that the outer surface of the control member interacts with the transition profile of the finger, whereby the inner surface of the finger is transferred on to the sliding surface, the stored energy in the finger then acting on the sliding surface thereby to exert a spring force for returning the sleeve to a needle shielding position.

2. A safety device as claimed in claim 1, wherein the finger is arranged to block movement of the sleeve when the sleeve has been returned to a needle shielding position by interengagement of the finger with said one of the sleeve and needle mount.

3. A safety device as claimed in claim 2, wherein said one of the sleeve and needle mount includes an abutment surface for interengagement with the finger and the control member is arranged to flex the finger clear of the abutment surface during initial movement of the sleeve from an initial position thereof.

4. A safety device as claimed in claim 1, wherein the inner surface of the finger provides a running surface in addition to the camming surface, and the camming surface is arranged to slide on the external surface of the control member and the running surface is arranged to slide on the sliding surface of said one of the sleeve and mount.

5. A safety device as claimed in claim 4, wherein there are two parallel and similar camming surfaces on the finger and the running surface is disposed between the camming surfaces, for at least part of the length of the running surface, or there are two parallel and similar running surfaces on the finger and the camming surface is disposed between the running surfaces, for at least part of the length of the camming surface.

6. A safety device as claimed in claim 1, wherein the needle mount is of a smaller diameter than the sleeve such that the sleeve slides over the needle mount, and the finger is carried by the sleeve to project rearwardly for contacting the control member and subsequently contacting the sliding surface of the needle mount.

7. A safety device as claimed in claim 6, wherein the needle mount has a bore for receiving a needle hub from which a needle projects forwardly, the hub being configured for connection to a syringe.

8. A safety device as claimed in claim 1, wherein a needle is supported directly in the needle mount so as to project forwardly therefrom.

9. A safety device as claimed in claim 1, wherein the needle mount is configured for direct mounting on a syringe having a needle secured thereto and projecting forwardly therefrom.

10. A safety device as claimed in claim 1, wherein one end of the finger or said first finger is mounted on the sleeve, and said part of the finger is disposed at or adjacent the other end of the finger and is configured to engage the abutment surface of the needle mount when the finger is in its undeformed condition.

11. A safety device as claimed in claim 1, wherein the control member is slidably carried within the sleeve and is held against rotation with respect thereto.

12. A safety device as claimed in claim 1, wherein there is a plurality of fingers spaced circumferentially around the sleeve or mount.

13. A safety device as claimed in claim 1, wherein the control member serves as an indicator to show whether the device is ready for use or has been used and the sleeve is blocked against sliding movement towards the non-shielding position.

14. A safety device as claimed in claim 13, wherein the control member is of a color which contrasts with that of the sleeve and needle mount.

15. A safety device as claimed in claim 13, wherein a window is provided in a forward part of the sleeve to which the control member is transferred when the sleeve is in its non-shielding position, whereby the control member may be observed through that window.

16. A safety device as claimed in claim 13, wherein at least part of the sleeve is of a translucent material whereby the position of the control member therewithin may be observed.

17. A safety needle assembly comprising a safety device as claimed in claim 1 in combination with a medical needle housed within the device and shielded by the sleeve when in its shielding position.

18. An injection device comprising a safety needle assembly as claimed in claim 17 in combination with a syringe or injector arranged to co-operate with the assembly to permit the performance of a medical procedure with the medical needle but imparting passive safety on the sharp tip of the needle.

19. A safety device for shielding a medical needle having a sharp tip, comprising:
a needle mount for directly or indirectly supporting the safety device with respect to the medical needle;
a needle shielding sleeve for surrounding the needle and arranged coaxially with the mount for sliding movement relative to the mount from an initial needle shielding position towards a non-shielding position whereat at least the tip of the needle is exposed beyond the sleeve;
an abutment surface and a sliding surface provided on one of the sleeve and mount;
at least one elongate resiliently flexible finger provided on the other of the sleeve and mount and serving as a spring to return the sleeve to a needle shielding position, the finger having a part for engaging the abutment surface to block movement of the sleeve to the non-shielding position when said part is aligned and engaged with the abutment surface, the finger further having an inner surface and an elongate camming surface provided on the inner surface; and
a control member having an outer surface and arranged coaxially with the sleeve and mount, the control member having an initial set position with respect to the finger and being slidably displaceable with respect to the finger from said set position when the sleeve slides from its initial position towards the non-shielding position;

wherein:
initial movement of the sleeve from its initial position displaces the control member from its initial set position with respect to the finger so that the outer surface of the control member interacts with the camming surface of the finger to flex the finger and thus move said part thereof out of alignment with the abutment surface to allow the sleeve to move towards the non-shielding position;
continued movement of the sleeve towards the non-shielding position causes continuing interaction between the control member and the camming surface to further increase the flexing of the finger so storing energy therein for returning the sleeve to a needle shielding position;
and thereafter further movement of the sleeve exposes more of the needle beyond the sleeve and the interaction between the outer surface of the control member and the camming surface causes the camming surface to transition onto the sliding surface, such that the camming surface bears on said sliding surface so that the energy stored within the finger exerts a spring force on the sleeve, to urge the sleeve to a needle shielding position whereat said finger part is aligned with the abutment surface to block movement of the sleeve towards the non-shielding position.

20. A safety device as claimed in claim 19, wherein the camming surface has an end remote from said part of the finger and there is a transition profile between the camming surface and the inner surface of the finger at said end of the camming surface.

21. A safety device as claimed in claim 20, wherein the transition profile comprises an edge at the end of the camming surface, whereby the camming surface comes off the control member outer surface with relatively little axial sleeve movement.

22. A safety device as claimed in claim 20, wherein the transition profile comprises a rounded or tapering surface extending along the length of the finger between the camming surface and the inner surface of the finger, whereby the camming surface slides off the control member outer surface when the transition profile slides on to the control member outer surface.

23. A safety device as claimed in claim 19, wherein the inner surface of the finger provides a running surface in addition to the camming surface, and the camming surface is arranged to slide on the external surface of the control member and the running surface is arranged to slide on the sliding surface of said one of the sleeve and mount.

24. A safety device as claimed in claim 23, wherein there are two parallel and similar camming surfaces on the finger and the running surface is disposed between the camming surfaces, for at least part of the length of the running surface, or there are two parallel and similar running surfaces on the finger and the camming surface is disposed between the running surfaces, for at least part of the length of the camming surface.

25. A safety device as claimed in claim 19, wherein the needle mount is of a smaller diameter than the sleeve such that the sleeve slides over the needle mount, and the finger is carried by the sleeve to project rearwardly for contacting the control member and subsequently contacting the sliding surface of the needle mount.

26. A safety device as claimed in claim 25, wherein the needle mount has a bore for receiving a needle hub from which a needle projects forwardly, the hub being configured for connection to a syringe.

27. A safety device as claimed in claim 19, wherein a needle is supported directly in the needle mount so as to project forwardly therefrom.

28. A safety device as claimed in claim 19, wherein the needle mount is configured for direct mounting on a syringe having a needle secured thereto and projecting forwardly therefrom.

29. A safety device for shielding a medical needle having a sharp tip, comprising:
- a needle mount for directly or indirectly supporting the safety device with respect to the medical needle;
- a needle shielding sleeve for surrounding the needle and arranged coaxially with the mount for sliding movement relative to the mount from an initial needle shielding position towards a non-shielding position whereat at least the tip of the needle is exposed beyond the sleeve;
- an abutment surface and a sliding surface provided on one of the sleeve and mount;
- at least one elongate resiliently flexible finger provided on the other of the sleeve and mount and serving as a spring to return the sleeve to a needle shielding position, the finger having a part for engaging the abutment surface to block movement of the sleeve to the non-shielding position when said part is aligned and engaged with the abutment surface, the finger further having an inner surface provided with an elongate camming surface and a transition profile between the camming surface and the inner surface; and
- a control member having an outer surface and arranged coaxially with the sleeve and mount, the control member having an initial set position with respect to the finger and being slidably displaceable with respect to the finger from said set position when the sleeve slides from its initial position towards the non-shielding position;

wherein:
- initial movement of the sleeve from its initial position displaces the control member from its initial set position with respect to the finger so that the outer surface of the control member interacts with the camming surface of the finger to flex the finger and thus move said part thereof out of alignment with the abutment surface to allow the sleeve to move towards the non-shielding position;
- continued movement of the sleeve towards the non-shielding position causes continuing interaction between the control member and the camming surface to further increase the flexing of the finger so storing energy therein for returning the sleeve to a needle shielding position;
- and thereafter further movement of the sleeve exposes more of the needle beyond the sleeve and the interaction between the outer surface of the control member interacts with the transition profile, so as to cause the inner surface of the finger to bear on said sliding surface so that the energy stored within the finger exerts a spring force on the sleeve, to urge the sleeve to a needle shielding position whereat said finger part is aligned with the abutment surface to block movement of the sleeve towards the non-shielding position.

* * * * *